(12) United States Patent
Liu et al.

(10) Patent No.: US 7,985,749 B2
(45) Date of Patent: Jul. 26, 2011

(54) COMPOUNDS AND COMPOSITIONS AS CATHEPSIN S INHIBITORS

(75) Inventors: Hong Liu, San Diego, CA (US); David C. Tully, San Diego, CA (US); Arnab Chatterjee, Encinitas, CA (US); Phillip B. Alper, Poway, CA (US); David H. Woodmansee, San Diego, CA (US); Daniel Mutnick, San Diego, CA (US)

(73) Assignee: Novartis AG, Basel (CH)

( * ) Notice: Subject to any disclaimer, the term of this patent is extended or adjusted under 35 U.S.C. 154(b) by 992 days.

(21) Appl. No.: 11/568,459

(22) PCT Filed: Apr. 29, 2005

(86) PCT No.: PCT/US2005/015117
§ 371 (c)(1),
(2), (4) Date: Nov. 29, 2006

(87) PCT Pub. No.: WO2005/107464
PCT Pub. Date: Nov. 17, 2005

(65) Prior Publication Data
US 2007/0232606 A1    Oct. 4, 2007

Related U.S. Application Data

(60) Provisional application No. 60/566,990, filed on Apr. 30, 2004.

(51) Int. Cl.
*A61K 31/5355* (2006.01)
*C07D 413/12* (2006.01)
(52) U.S. Cl. .............. 514/233.8; 544/127; 544/135; 544/137; 544/138; 546/198; 548/217; 514/236.8; 514/321; 514/375
(58) Field of Classification Search ............. 544/127, 544/135, 137, 138; 546/198; 548/217; 514/233.8, 514/234.2, 321, 375
See application file for complete search history.

(56) References Cited

U.S. PATENT DOCUMENTS 6,562,827 B1    5/2003    Lubisch et al. .......... 514/252.13

FOREIGN PATENT DOCUMENTS

| WO | WO 02/07270 A2 | 1/2002 |
| WO | WO 02/100849 A2 | 12/2002 |
| WO | 03/024924 | 3/2003 |
| WO | WO 03/105855 A1 | 12/2003 |

OTHER PUBLICATIONS

Supplementary European Search Report, Application No. 05742278.4, Jun. 16, 2009, 5 pgs.

*Primary Examiner* — Bernard Dentz
(74) *Attorney, Agent, or Firm* — Paul D. Strain; Strain & Strain PLLC

(57) ABSTRACT

The invention provides compounds, pharmaceutical compositions comprising such compounds and methods of using such compounds to treat or prevent diseases or disorders associated with the activity of Cathepsin S.

9 Claims, No Drawings

COMPOUNDS AND COMPOSITIONS AS CATHEPSIN S INHIBITORS

This application claims benefit of U.S. Provisional Application No. 60/566,990, filed Apr. 30, 2004, which in its entirety is herein incorporated by reference.

CROSS-REFERENCE TO RELATED APPLICATIONS

This application claims the benefit of priority to U.S. Provisional Patent Application No. 60/566,990, filed 30 Apr. 2004. The full disclosure of this application is incorporated herein by reference in its entirety and for all purposes.

BACKGROUND OF THE INVENTION

1. Field of the Invention

The invention provides compounds, pharmaceutical compositions comprising such compounds and methods of using such compounds to treat or prevent diseases or disorders associated with the activity of Cathepsin S.

2. Background

Cysteine proteases represent an enzymatic class of proteins that catalyze the hydrolysis of peptide bonds by a nucleophilic sulfhydryl group of a cysteine residue in the active site of the enzyme. Cathepsins are a subclass of cysteine protease that play a major role in lysosomal, endosomal, and extracellular protein degradation and have thus been implicated in many disease processes. Cathepsin S [EC 3.4.22.27] has been shown to be required for proper MHC class II antigen presentation. As a result of its non-redundant role in MHC class II antigen presentation, cathepsin S has been associated with several normal and disease processes in mammals. These diseases or disorders include, but are not limited to: osteoporosis, osteoarthritis, muscular dystrophy, inflammation, tumor invasion, glomerulonephritis, malaria, periodontal disease, metachromatic leukodystrophy, periodontal diseases, Paget's disease, atherosclerosis, multiple sclerosis, rheumatoid arthritis, juvenile onset diabetes, lupus, asthma, tissue rejection, Alzheimer's disease, Parkinson's disease, neuronal degeneration, shock, cancer, malaria, neuropathic pain, COPD, inflammatory bowel disease, allergy, Chagas, leishmaniasis, shistosomiasis, and African trypanosomiasis.

The novel compounds of this invention inhibit the activity of cathepsin S and are, therefore, expected to be useful in the treatment of cathepsin S-associated diseases.

SUMMARY OF THE INVENTION

In one aspect, the present invention provides compounds of Formula I:

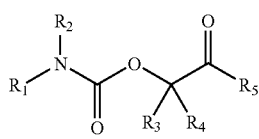

in which
$R_1$ is chosen from formula (a), (b) and (c):

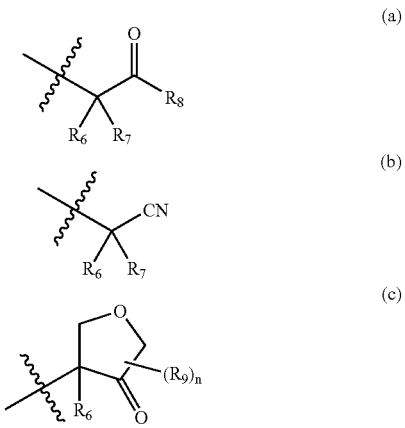

wherein n is an integer selected from 0, 1 and 2;
$R_6$ and $R_7$ are independently chosen from hydrogen, $C_{1-6}$alkyl, cyano-$C_{0-6}$alkyl, $C_{3-12}$cycloalkyl$C_{0-4}$alkyl and $C_{6-10}$aryl$C_{0-4}$alkyl; or $R_6$ and $R_7$ together with the carbon atom to which $R_6$ and $R_7$ are attached form $C_{3-8}$heterocycloalkyl or $C_{3-12}$cycloalkyl;
wherein any alkyl of $R_6$ and $R_7$ can optionally have a methylene replaced with an atom or group chosen from O and $S(O)_{0-2}$; wherein any aryl, heterocycloalkyl or cycloalkyl of $R_6$, $R_7$ or formed by the combination of $R_6$ and $R_7$ can be optionally substituted with 1 to 3 radicals independently selected from halo, hydroxy, nitro, cyano, $C_{1-6}$alkyl, $C_{1-6}$alkoxy, halo-substituted-$C_{1-6}$alkyl, halo-substituted-$C_{1-6}$alkoxy, —XC(O)OR$_{10}$, —X(S(O)$_{0-2}$R$_{10}$, —XNRS(O)$_{0-2}$R$_{10}$ and —XS(O)$_{0-2}$NR$_{10}$R$_{10}$; wherein X is a bond or $C_{1-4}$alkylene; and $R_{10}$ is independently chosen from hydrogen and $C_{1-6}$alkyl;
$R_8$ is chosen from hydrogen, $C_{6-10}$aryl$C_{0-4}$alkyl, $C_{5-10}$heteraryl$C_{0-4}$alkyl, —C(O)OR$_{10}$ and —C(O)NR$_{10}$R$_{11}$; wherein $R_{10}$ is chosen from hydrogen and $C_{1-6}$alkyl; and $R_{11}$ is chosen from hydrogen, $C_{1-6}$alkyl and —[CR$_{12}$R$_{13}$]$_m$-R$_{14}$; wherein m is chosen from 0, 1 and 2; $R_{12}$ and $R_{13}$ are independently chosen from hydrogen and $C_{1-6}$alkyl; and $R_{14}$ is selected from $C_{6-10}$aryl, $C_{5-10}$heteroaryl, $C_{3-12}$cycloalkyl and $C_{3-8}$heterocycloalkyl;
wherein any aryl, heteroaryl, cycloalkyl or heterocycloalkyl of $R_8$ and $R_{14}$ can be optionally substituted by 1 to 3 radicals independently chosen from halo, hydroxy, nitro, cyano, $C_{1-6}$alkyl, $C_{1-6}$alkoxy, halo-substituted-$C_{1-6}$alkyl, halo-substituted-$C_{1-6}$alkoxy, $C_{6-10}$aryl, $C_{5-10}$heteraryl, $C_{3-12}$cycloalkyl and $C_{3-8}$heterocycloalkyl; and
$R_9$ is chosen from $C_{1-6}$alkyl, $C_{6-10}$aryl$C_{0-4}$alkyl and $C_{3-12}$cycloalkyl$C_{0-4}$alkyl;
$R_2$ is chosen from hydrogen and $C_{1-6}$alkyl;
$R_3$ and $R_4$ are independently chosen from hydrogen, $C_{1-6}$alkyl, $C_{3-12}$cycloalkyl$C_{0-4}$alkyl and $C_{6-10}$aryl$C_{0-4}$alkyl; wherein any alkyl of $R_3$ and $R_4$ can optionally have a methylene replaced with an atom or group chosen from O and $S(O)_{0-2}$; wherein any aryl or cycloalkyl of $R_3$ and $R_4$ can optionally be substituted with 1 to 3 radicals independently chosen from halo, hydroxy, nitro, cyano, $C_{1-6}$alkyl, $C_{1-6}$alkoxy, halo-substituted-$C_{1-6}$alkyl and halo-substituted-$C_{1-6}$alkoxy;
$R_5$ is chosen from $C_{3-8}$heterocycloalkyl and NR$_{12}$R$_{13}$, wherein $R_{12}$ and $R_{13}$ are independently chosen from hydrogen and $C_{1-6}$alkyl; wherein any heterocycloalkyl of $R^5$ can be optionally substituted with 1 to 3 radicals independently selected from halo, hydroxy, nitro, cyano, $C_{1-6}$alkyl, $C_{1-6}$alkoxy, halo-substituted-$C_{1-6}$alkyl, halo-substituted-$C_{1-6}$alkoxy, —XC(O)OR$_{10}$, —X(S(O))$_{0-2}$R$_{10}$, —XNR$_{10}$S(O)$_{0-2}$R$_{10}$ and —XS(O)$_{0-2}$NR$_{10}$R$_{10}$; wherein X is a bond or $C_{1-4}$alkylene; and R$_{10}$ is independently chosen from hydrogen and $C_{1-6}$alkyl; and the N-oxide derivatives, prodrug derivatives, protected derivatives, individual isomers and mixture of isomers thereof; and the pharmaceutically acceptable salts and solvates (e.g. hydrates) of such compounds.

In a second aspect, the present invention provides a pharmaceutical composition which contains a compound of Formula I or a N-oxide derivative, individual isomers and mixture of isomers thereof; or a pharmaceutically acceptable salt thereof, in admixture with one or more suitable excipients.

In a third aspect, the present invention provides a method of treating a disease in an animal in which inhibition of cathepsin S activity can prevent, inhibit or ameliorate the pathology and/or symptomology of the diseases, which method comprises administering to the animal a therapeutically effective amount of a compound of Formula I or a N-oxide derivative, individual isomers and mixture of isomers thereof, or a pharmaceutically acceptable salt thereof.

In a fourth aspect, the present invention provides the use of a compound of Formula I in the manufacture of a medicament for treating a disease in an animal in which cathepsin S activity contributes to the pathology and/or symptomology of the disease.

In a fifth aspect of the present invention, compounds of Formula I selectively inhibit cathepsin S relative to cathepsin K, L, B, or combinations thereof.

In a sixth aspect, the present invention provides a process for preparing compounds of Formula I and the N-oxide derivatives, prodrug derivatives, protected derivatives, individual isomers and mixture of isomers thereof, and the pharmaceutically acceptable salts thereof.

DETAILED DESCRIPTION OF THE INVENTION

Definitions

"Alkyl" as a group and as a structural element of other groups, for example halo-substituted-alkyl and alkoxy, can be either straight-chained or branched. $C_{1-6}$alkoxy includes, methoxy, ethoxy, and the like. Halo-substituted alkyl includes trifluoromethyl, pentafluoroethyl, and the like.

"Aryl" means a monocyclic or fused bicyclic aromatic ring assembly containing six to ten ring carbon atoms. For example, aryl can be phenyl or naphthyl, preferably phenyl. "Arylene" means a divalent radical derived from an aryl group. "Heteroaryl" is as defined for aryl where one or more of the ring members are a heteroatom. For example heteroaryl includes pyridyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, etc. "$C_{6-10}$aryl$C_{0-4}$alkyl" means an aryl as described above connected via a alkylene grouping. For example, $C_{6-10}$aryl$C_{0-4}$ alkyl includes phenethyl, benzyl, etc.

"Cycloalkyl" means a saturated or partially unsaturated, monocyclic, fused bicyclic, bridged polycyclic ring assembly or spiro ring assembly (where two rings share a common atom, for example, spiro[5.5]undecane, and the like) containing the number of ring atoms indicated. For example, $C_{3-10}$cycloalkyl includes cyclopropyl, cyclobutyl, cyclopentyl, cyclohexyl, etc. "Heterocycloalkyl" means cycloalkyl, as defined in this application, provided that one or more of the ring carbons indicated, are replaced by a moiety selected from —O—, —N—, —NR—, —C(O)—, —S—, —S(O)— or —S(O)$_2$—, wherein R is hydrogen, $C_{1-4}$alkyl or a nitrogen protecting group. For example, $C_{3-8}$heterocycloalkyl as used in this application to describe compounds of the invention includes morpholino, pyrrolidinyl, piperazinyl, piperidinyl, piperidinylone, 1,4-dioxa-8-aza-spiro[4.5]dec-8-yl, etc.

"Halogen" (or halo) preferably represents chloro or fluoro, but can also be bromo or iodo.

"Treat", "treating" and "treatment" refer to a method of alleviating or abating a disease and/or its attendant symptoms.

DESCRIPTION OF THE PREFERRED EMBODIMENTS

The present invention provides compounds, compositions and methods for the treatment of diseases in which inhibition of cathepsin S activity can prevent, inhibit or ameliorate the pathology and/or symptomology of the diseases, which method comprises administering to the animal a therapeutically effective amount of a compound of Formula I.

In one embodiment are compounds of Formula Ia:

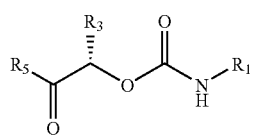

Ia in which
R$_1$ is chosen from formula (a), (b) and (c):

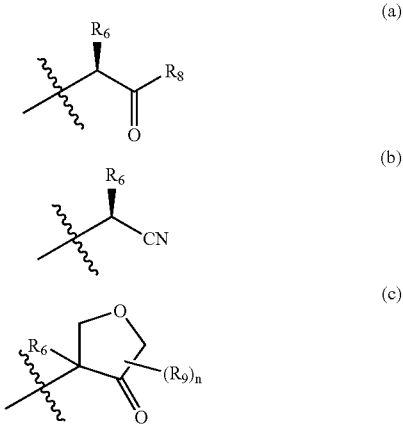

wherein n is an integer selected from 0, 1 and 2;
R$_6$ is chosen from hydrogen, $C_{1-6}$alkyl, cyano-$C_{0-6}$alkyl, $C_{3-12}$cycloalkyl$C_{0-4}$alkyl and $C_{6-10}$aryl$C_{0-4}$alkyl;
wherein any alkyl of R$_6$ can optionally have a methylene replaced with an atom or group chosen from O and S(O)$_{0-2}$; wherein any aryl or cycloalkyl of R$_6$ can be optionally substituted with 1 to 3 radicals independently selected from halo, hydroxy, nitro, cyano, $C_{1-6}$alkyl, $C_{1-6}$alkoxy, halo-substituted-$C_{1-6}$alkyl, halo-substituted-$C_{1-6}$alkoxy, —XC(O)OR$_{10}$, —X(S(O))$_{0-2}$R$_{10}$, —XNRS(O)$_{0-2}$R$_{10}$ and —XS(O)$_{0-2}$NR$_{10}$R$_{10}$; wherein X is a bond or C$_{1-4}$alkylene; and R$_{10}$ is independently chosen from hydrogen and C$_{1-6}$alkyl;

R$_8$ is chosen from hydrogen, C$_{6-10}$arylC$_{0-4}$alkyl, C$_{5-10}$heterarylC$_{0-4}$alkyl, —C(O)OR$_{10}$ and —C(O)NR$_{10}$R$_{11}$; wherein R$_{10}$ is chosen from hydrogen and C$_{1-6}$alkyl; and R$_{11}$ is chosen from hydrogen, C$_{1-6}$alkyl and —[CR$_{12}$R$_{13}$]$_m$-R$_{14}$; wherein m is chosen from 0, 1 and 2; R$_{12}$ and R$_{13}$ are independently chosen from hydrogen and C$_{1-6}$alkyl; and R$_{14}$ is selected from C$_{6-10}$aryl, C$_{5-10}$heteroaryl, C$_{3-12}$cycloalkyl and C$_{3-8}$heterocycloalkyl;

wherein any aryl, heteroaryl, cycloalkyl or heterocycloalkyl of R$_8$ and R$_{14}$ can be optionally substituted by 1 to 3 radicals independently chosen from halo, hydroxy, nitro, cyano, C$_{1-6}$alkyl, C$_{1-6}$alkoxy, halo-substituted-C$_{1-6}$alkyl, halo-substituted-C$_{1-6}$alkoxy, C$_{6-10}$aryl, C$_{5-10}$heteraryl, C$_{3-12}$cycloalkyl and C$_{3-8}$heterocycloalkyl; and R$_9$ is chosen from C$_{1-6}$alkyl, C$_{6-10}$arylC$_{0-4}$alkyl and C$_{3-12}$cycloalkylC$_{0-4}$alkyl;

R$_3$ is chosen from hydrogen, C$_{1-6}$alkyl, C$_{3-12}$cycloalkylC$_{0-4}$alkyl and C$_{6-10}$arylC$_{0-4}$alkyl; wherein any alkyl of R$_3$ can optionally have a methylene replaced with an atom or group chosen from O and S(O)$_{0-2}$; wherein any aryl or cycloalkyl of R$_3$ can optionally be substituted with 1 to 3 radicals independently chosen from halo, hydroxy, nitro, cyano, C$_{1-6}$alkyl, C$_{1-6}$alkoxy, halo-substituted-C$_{1-6}$alkyl and halo-substituted-C$_{1-6}$alkoxy;

R$_5$ is chosen from C$_{3-8}$heterocycloalkyl and NR$_{12}$R$_{13}$, wherein R$_{12}$ and R$_{13}$ are independently chosen from hydrogen and C$_{1-6}$alkyl; wherein any heterocycloalkyl of R$^5$ can be optionally substituted with 1 to 3 radicals independently selected from halo, hydroxy, nitro, cyano, C$_{1-6}$alkyl, C$_{1-6}$alkoxy, halo-substituted-C$_{1-6}$alkyl, halo-substituted-C$_{1-6}$alkoxy, —XC(O)OR$_{10}$, —X(S(O)$_{0-2}$R$_{10}$, —XNR$_{10}$S(O)$_{0-2}$R$_{10}$ and —XS(O)$_{0-2}$NR$_{10}$R$_{10}$; wherein X is a bond or C$_{1-4}$alkylene; and R$_{10}$ is independently chosen from hydrogen and C$_{1-6}$alkyl.

In another embodiment, R$_2$ and R$_4$ are both hydrogen; R$_6$ is chosen from hydrogen, C$_{1-6}$alkyl, cyano-C$_{0-6}$alkyl, C$_{3-12}$cycloalkylC$_{0-4}$alkyl and C$_{6-10}$arylC$_{0-4}$alkyl; wherein any alkyl of R$_6$ can optionally have a methylene replaced with an atom or group chosen from O and S(O)$_{0-2}$; wherein any aryl or cycloalkyl of R$_6$ can be optionally substituted with 1 to 3 radicals independently selected from halo;

R$_7$ is hydrogen;

R$_8$ is C$_{5-10}$heteraryl optionally substituted by 1 to 3 radicals independently chosen from halo, C$_{1-6}$alkyl, halo-substituted-C$_{1-6}$alkyl, C$_{6-10}$aryl, C$_{5-10}$heteraryl, C$_{3-12}$cycloalkyl and C$_{3-8}$heterocycloalkyl; and R$_9$ is C$_{1-6}$alkyl;

R$_3$ is chosen from C$_{1-6}$alkyl, C$_{3-12}$cycloalkylC$_{0-4}$alkyl and C$_{6-10}$arylC$_{0-4}$alkyl; wherein any alkyl of R$_3$ can optionally have a methylene replaced with an atom or group chosen from O and S(O)$_{0-2}$;

R$_5$ is chosen from C$_{3-8}$heterocycloalkyl and —NR$_{12}$R$_{13}$, wherein R$_{12}$ and R$_{13}$ are independently chosen from hydrogen and C$_{1-6}$alkyl.

In a further embodiment, R$_6$ is chosen from hydrogen, methyl, ethyl propyl, isopropyl, cyclopropyl, cyanomethyl, 2-chloro-benzyloxymethyl, benzyloxymethyl, benzyloxyethyl, phenethyl and benzyl.

In another embodiment, R$_8$ is benzooxazol-2-yl, benzothiazol-2-yl, [1,2,4]oxadiazol-3-yl, [1,2,4]oxadiazol-5-yl and oxazolo[5,4-b]pyridin-2-yl; wherein any heteroaryl of R$_8$ is optionally substituted by 1 to 3 radicals independently chosen from halo, ethyl, phenyl, cyclopropyl and trifluoromethyl.

In another embodiment, R$_3$ is selected from cyclohexyl-methyl, cyclopentyl-methyl, benzyl-sulfonyl-methyl, cyclohexyl-ethyl, phenyl, iso-butyl, t-butyl-methyl, cyclohexyl, benzyl, and phenethyl; and R$_5$ is chosen from morpholino, dimethylamino, piperidinyl and pyrrolidinyl.

Preferred compounds of Formula I are detailed in the Examples and Table I, infra, and selected from 2-cyclohexyl-(1S)-(morpholine-4-carbonyl)ethyl 2-(benzoxazol-2-yl)-(1S)-cyclopropyl-2-oxo-ethyl carbamate, 2-phenylmethane-sulfonyl-(1R)-(morpholine-4-carbonyl)ethyl 2-(benzoxazol-2-yl)-(1S)-methyl-2-oxo-ethyl carbamate, 2-cyclohexyl-(1S)-(morpholine-4-carbonyl)ethyl (1S)-(5-ethyl-[1,2,4]oxadiazole-3-carbonyl)propyl carbamate, 2-cyclohexyl-(1S)-(morpholine-4-carbonyl)ethyl (1S)-(5-phenyl-[1,2,4]oxadiazole-3-carbonyl)propyl carbamate, 2-cyclohexyl-(1S)-(morpholine-4-carbonyl)ethyl 4-oxo-tetrahydro-furan-(3S)-yl carbamate, (S)-1-tert-Butoxycarbonyl-4-cyano-4-(1-cyclohexylmethyl-2-morpholin-4-yl-2-oxo-ethoxycarbonylamino)-piperidine, (S)-4-Cyano-4-(1-cyclohexylmethyl-2-morpholin-4-yl-2-oxo-ethoxycarbonylamino)-1-methyl-piperidine, (1S)-cyclohexylmethyl-2-morpholin-4-yl-2-oxo-ethyl 2-(2-chloro-benzyloxy)-(1R)-cyano-ethyl carbamate, 2-cyclohexyl-(1S)-(morpholine-4-carbonyl)ethyl 2-(benzoxazol-2-yl)-(1S)-methyl-2-oxo-ethyl carbamate, 2-cyclohexyl-(1S)-(morpholine-4-carbonyl)ethyl (1S)-(benzoxazole-2-carbonyl)-propyl carbamate, 2-cyclohexyl-(1S)-(morpholine-4-carbonyl)ethyl (1S)-(benzoxazole-2-carbonyl)-butyl carbamate, 2-cyclohexyl-(1S)-(morpholine-4-carbonyl)ethyl 2-(5-fluoro-benzoxazol-2-yl)-(1S)-methyl-2-oxo-ethyl carbamate, 2-cyclohexyl-(1S)-(morpholine-4-carbonyl)ethyl 2-(6-fluoro-benzoxazol-2-yl)-(1S)-methyl-2-oxo-ethyl carbamate, 2-cyclohexyl-(1S)-(morpholine-4-carbonyl)ethyl (1S)-(benzoxazole-2-carbonyl)-2-methyl-propyl carbamate, 2-cyclopentyl-(1S)-(morpholine-4-carbonyl)ethyl (1S)-(benzoxazole-2-carbonyl)-propyl carbamate, 2-cyclohexyl-(1S)-(morpholine-4-carbonyl) ethyl (1S)-(benzothiazole-2-carbonyl)-propyl carbamate, 2-cyclohexyl-(1S)-(morpholine-4-carbonyl)ethyl (1S)-(benzothiazole-2-carbonyl)-ethyl carbamate, 2-phenylmethane-sulfonyl-(1R)-(morpholine-4-carbonyl)ethyl (1S)-(benzoxazole-2-carbonyl)-propyl carbamate, 3-cyclohexyl-(1S)-(morpholine-4-carbonyl)propyl (1S)-(benzoxazole-2-carbonyl)-ethyl carbamate, 3-cyclohexyl-(1S)-(morpholine-4-carbonyl)propyl (1S)-(benzoxazole-2-carbonyl)-propyl carbamate, (1S)-(morpholine-4-carbonyl)-1-phenyl-methyl (1S)-(benzoxazole-2-carbonyl)-propyl carbamate, 3,3-dimethyl-(1S) -(morpholine-4-carbonyl)-butyl (1S)-(benzoxazole-2-carbonyl)-propyl carbamate, (1S)-cyclohexyl-1-(morpholine-4-carbonyl)-methyl (1S)-(benzoxazole-2-carbonyl)-propyl carbamate, (1S)-cyclohexylmethyl-2-oxo-2-(piperidin-1-yl)-ethyl (1S)-(benzoxazole-2-carbonyl)-ethyl carbamate, (1S)-cyclohexylmethyl-2-oxo-2-(pyrrolidin-1-yl)-ethyl 2-(benzoxazol-2-yl)-(1S)-cyclopropyl-2-oxo-ethyl carbamate, (1S)-cyclohexylmethyl-2-oxo-2-(pyrrolidin-1-yl)-ethyl (1S)-(benzoxazole-2-carbonyl)-propyl carbamate, (1S)-cyclohexylmethyl-2-oxo-2-(pyrrolidin-1-yl)-ethyl (1S)-(benzoxazole-2-carbonyl)-butyl carbamate, 2-cyclohexyl-(1S)-(morpholine-4-carbonyl)ethyl 4-oxo-tetrahydro-furan-(3R)-yl carbamate, (1S-cyclohexylmethyl-2-(morpholin-4-yl)-2-oxo-ethyl (1S)-cyano-2-methyl-propyl carbamate, (1S)-cyclohexylmethyl-2-(morpholin-4-yl)-2-oxo-ethyl (1S)-cyano-propyl carbamate, (1S)-cyclohexylmethyl-2-(morpholin-4-yl)-2-oxo-ethyl 2-benzyloxy-(1R)-cyano-ethyl carbamate, (1S)-cyclohexyl-methyl-2-(morpholin-4-yl)-2-oxo-ethyl 3-benzyloxy-(1S)-cyano-propyl carbamate, (1S)-cyclohexylmethyl-2-(morpholin-4-yl)-2-oxo-ethyl (1S)-cyano-3-phenyl-propyl carbamate, (1)-cyclohexylmethyl-2-(morpholin-4-yl)-2-oxo-ethyl (1S),2-dicyano-ethyl carbamate, (1S)-cyclohexylmethyl-2-(morpholin-4-yl)-2-oxo-ethyl (1S)-cyano-2-phenyl-ethyl carbamate, (1S)-cyclohexylmethyl-2-(morpholin-4-yl)-2-oxo-ethyl cyanomethyl carbamate, 2-cyclohexyl-(1S)-(morpholine-4-carbonyl)ethyl (1S)-(6-fluoro-benzoxazole-2-carbonyl)-propyl carbamate, 2-cyclopentyl-(1S)-(morpholine-4-carbonyl)ethyl (1S)-(6-fluoro-benzoxazole-2-carbonyl)-propyl carbamate, 2-cyclohexyl-(1S)-(morpholine-4-carbonyl)ethyl (1S)-(oxazolo[5,4-b]pyridine-2-carbonyl)-propyl carbamate, 2-cyclohexyl-(1S)-(morpholine-4-carbonyl)ethyl (1S)-cyclopropyl-2-(6-fluoro-benzoxazol-2-yl)-2-oxo-ethyl carbamate, (1S)-cyclohexyl-1-(morpholine-4-carbonyl)methyl (1S)-(6-fluoro-benzoxazole-2-carbonyl)-ethyl carbamate, (1S)-cyclohexyl-1-(morpholine-4-carbonyl)methyl (1S)-(6-fluoro-benzoxazole-2-carbonyl)-propyl carbamate, 2-cyclohexyl-(1S)-dimethylcarbamoyl-ethyl (1S)-(benzoxazole-2-carbonyl)-propyl carbamate, 2-cyclohexyl-(1S)-(morpholine-4-carbonyl)ethyl (1S)-(6-fluoro-benzoxazole-2-carbonyl)-butyl carbamate, 2-cyclohexyl-(1S)-(morpholine-4-carbonyl)ethyl (1S)-(5-cyclopropyl-[1,2,4]oxadiazole-3-carbonyl)-propyl carbamate, (1S)-cyclohexyl-1-(morpholine-4-carbonyl)methyl (1S)-(benzoxazole-2-carbonyl)-butyl carbamate, 2-cyclohexyl-(1S)-(morpholine-4-carbonyl)ethyl (1S)-(6-methyl-benzoxazole-2-carbonyl)-propyl carbamate, 2-cyclohexyl-(1S)-(morpholine-4-carbonyl)ethyl (1S)-(5-chloro-benzoxazole-2-carbonyl)-propyl carbamate, (1S)-(morpholine-4-carbonyl)-2-phenyl-ethyl (1S)-(benzoxazole-2-carbonyl)-propyl carbamate, (1S)-(morpholine-4-carbonyl)-3-phenyl-ethyl (1S)-(benzoxazole-2-carbonyl)-propyl carbamate, (1S)-cyclohexylmethyl-2-oxo-2-(pyrrolidin-1-yl)-ethyl (1S)-(7-fluoro-benzoxazole-2-carbonyl)-propyl carbamate, 2-cyclohexyl-(1S)-(morpholine-4-carbonyl)ethyl (1S)-(5-trifluoromethyl-[1,2,4]oxadiazole-3-carbonyl)-propyl carbamate, 2-cyclohexyl-(1S)-(morpholine-4-carbonyl)ethyl (1S)-(7-fluoro-benzoxazole-2-carbonyl)-propyl carbamate, 2-cyclohexyl-(1S)-(morpholine-4-carbonyl)ethyl (1S)-(5-fluoro-benzoxazole-2-carbonyl)-butyl carbamate; (1S)-cyclohexylmethyl-2-oxo-2-(pyrrolidin-1-yl)-ethyl (1S)-(6-fluoro-benzoxazole-2-carbonyl)-propyl carbamate; 2-cyclohexyl-(1S)-(morpholine-4-carbonyl)ethyl (1S)-(3-cyclopropyl-[1,2,4]oxadiazole-5-carbonyl)-propyl carbamate; 2-cyclohexyl-(1S)-(morpholine-4-carbonyl)ethyl (1R)-(5-cyclopropyl-[1,2,4]oxadiazole-3-carbonyl)-propyl carbamate; (S,S)-[1-(Benzooxazole-2-carbonyl)-propyl]-carbamic acid 3-methyl-1-(morpholine-4-carbonyl)-butyl ester; (S,S)-(2-Benzooxazol-2-yl-1-methyl-2-oxo-ethyl)-carbamic acid 3-methyl-1-(morpholine-4-carbonyl)-butyl ester; (S,S)-[1-(5-Cyclopropyl-[1,2,4]oxadiazole-3-carbonyl)-propyl]-carbamic acid 3,3-dimethyl-1-(pyrrolidine-1-carbonyl)-butyl ester; and (S,S)-[1-(5-Cyclopropyl-[1,2,4]oxadiazole-3-carbonyl)-propyl]-carbamic acid 3,3-dimethyl-1-(morpholine-4-carbonyl)-butyl ester.

Pharmacology and Utility

Compounds of the invention inhibit the activity of cathepsin S and, as such, are useful for treating diseases or disorders in which cathepsin S contribute to the pathology and/or symptomology of the disease. This invention further provides compounds of this invention for use in the preparation of medicaments for the treatment of diseases or disorders in which cathepsin S contributes to the pathology and/or symptomology of the disease. Cathepsin S mediated diseases or conditions include, but are not limited to: muscular dystrophy, inflammation, tumor invasion, glomerulonephritis, periodontal disease, neuropathic pain, COPD, inflammatory bowel disease, allergy, metachromatic leukodystrophy, osteoporosis, osteoarthritis (Inui, T., O. Ishibashi, *J Biol Chem* 1997, 272(13), 8109-12; Saftig, P., E. Hunziker, et al., *Adv Exp Med Biol* 2000+*ADs* 2000, 477, 293-303; Saftig, P., E. Hunziker, et al., *Proc Natl Acad Sci USA* 1998, 95(23), 13453-8), periodontal diseases, Paget's disease, atherosclerosis (Jormsjo, S., D. M. Wuttge, et al., *Am J Pathol* 2002 161(3), 939-45), multiple sclerosis (Beck, H., G. Schwarz, et al., *Eur J Immunol* 2001, 31(12), 3726-36), rheumatoid arthritis (Nakagawa, T. Y., W. H. Brissette, et al., *Immunity* 1999, 10(2), 207-17; Hou, W. S., Z. Li, et al., *Am J Pathol* 2001, 159(6), 2167-77), juvenile onset diabetes, lupus, asthma (Cimerman, N., P. M. Brguljan, et al., *Pflugers Arch* 2001, 442(6 Suppl 1), R204-6), tissue rejection, Alzheimer's disease (Lemere, C. A., J. S. Munger, et al., *Am J Pathol* 1995, 146(4), 848-60), Parkinson's disease (Liu, Y., L. Fallon, et al., *Cell* 2002, 111(2), 209-18), neuronal degeneration, shock (Jaeschke, H., M. A. Fisher, et al., *J Immunol* 1998, 160(7), 3480-6), cancer (Fernandez, P. L., X. Farre, et al., *Int J Cancer* 2001, 95(1), 51-5), malaria (alhotra, P., P. V. Dasaradhi, et al., *Mol Microbiol* 2002, 45(5), 1245-54), Chagas (Eakin, A. E., A. A. Mills, et al., *J Biol Chem* 1992, 267(11), 7411-20), leishmaniasis, shistosomiasis, and African trypanosomiasis (Caffrey, C. R., S. Scory, et al., *Curr Drug Targets* 2000, 1(2), 155-62; Lalmanach, G., A. Boulange, et al., *Biol Chem* 2002, 383(5), 739-49).

Foregoing, the present invention further provides a method for preventing or treating any of the diseases or disorders described above in a subject in need of such treatment, which method comprises administering to said subject a therapeutically effective amount (See, "*Administration and Pharmaceutical Compositions*", infra) of a compound of Formula I or a pharmaceutically acceptable salt thereof For any of the above uses, the required dosage will vary depending on the mode of administration, the particular condition to be treated and the effect desired.

Administration and Pharmaceutical Compositions

In general, compounds of the invention will be administered in therapeutically effective amounts via any of the usual and acceptable modes known in the art, either singly or in combination with one or more therapeutic agents. A therapeutically effective amount can vary widely depending on the severity of the disease, the age and relative health of the subject, the potency of the compound used and other factors. In general, satisfactory results are indicated to be obtained systemically at daily dosages of from about 0.03 to 10.0 mg/kg body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrollidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions can be sterilized and/or contain adjuvants, such as preserving, stabilizing, wetting or emulsifying agents, solution promoters, salts for regulating the osmotic pressure and/or buffers. In addition, they can also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations can also be used. Suitable formulations for topical application, e.g., to the skin and eyes, are preferably aqueous solutions, ointments, creams or gels well-known in the art. Such can contain solubilizers, stabilizers, tonicity enhancing agents, buffers and preservatives.

Compounds of the invention can be administered in therapeutically effective amounts in combination with one or more therapeutic agents (pharmaceutical combinations). For example, synergistic effects can occur with other substances used in the treatment of osteoporosis, osteoarthritis, muscular dystrophy, inflammation, tumor invasion, glomerulonephritis, malaria, periodontal disease, metachromatic leukodystrophy, periodontal diseases, Paget's disease, atherosclerosis, multiple sclerosis, rheumatoid arthritis, juvenile onset diabetes, lupus, asthma, tissue rejection, Alzheimer's disease, Parkinson's disease, neuronal degeneration, shock, cancer, malaria, neuropathic pain, COPD, inflammatory bowel disease, allergy, Chagas, leishinaniasis, shistosomiasis, and/or African trypanosomiasis. Where the compounds of the invention are administered in conjunction with other therapies, dosages of the co-administered compounds will of course vary depending on the type of co-drug employed, on the specific drug employed, on the condition being treated and so forth.

The invention also provides for a pharmaceutical combinations, e.g. a kit, comprising a) a first agent which is a compound of the invention as disclosed herein, in free form or in pharmaceutically acceptable salt form, and b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a co-agent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

Processes for Making Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

In the following schemes, several methods of preparing the compounds of the present invention are illustrative. One of skill in the art will appreciate that these methods are representative, and in no way inclusive of all methods for preparing the compounds of the present invention. The radicals in the schemes are as described in Formula I.

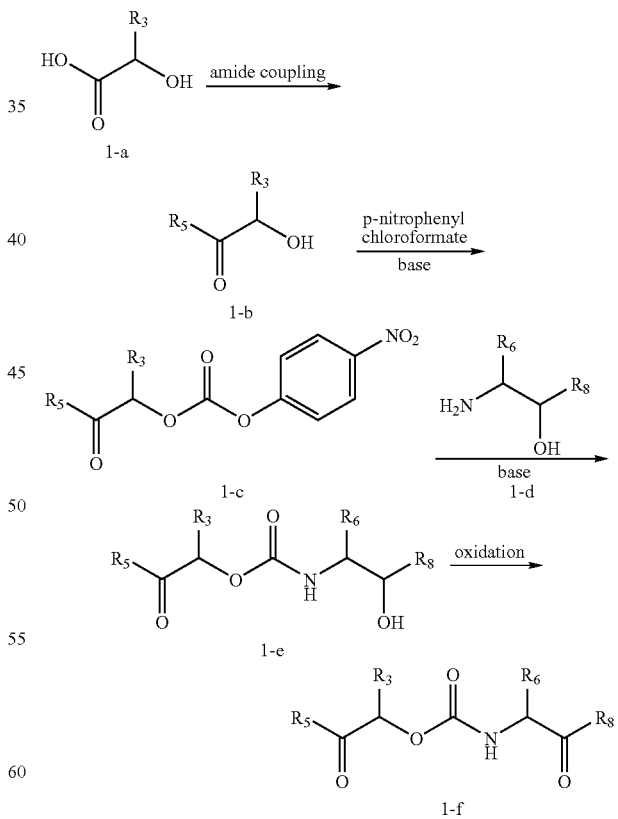

An illustration of the synthesis of the compounds in the present invention, in which $R_1$ is —$CR_7R_6C(\!=\!O)R_8$, and $R_2$, $R_4$ and $R_7$ are hydrogen, is given in Scheme 1. J. W. Kelly et al., Org. Lett., 2004, 6, 497, reviews various synthetic methods of α-hydroxy acids. The α-hydroxy acid 1-a is reacted with an amine R₅H under standard amide formation conditions (e.g. DIC/HOBt, HATU, PyBOP and etc.) to provide 1-b. For reviews of amide coupling reactions, see A. R. Chamberlin et al. *Chem. Rev.* 1997, 97, 2243 and M. Bodanszky, et al., The practice of peptide synthesis, 2$^{nd}$ Ed., Springer-Verlag 1994. 1-b is treated with p-nitrophenyl chloroformate under basic conditions yielding the mixed carbonate 1-c. The reaction of 1-c with NH₂CHR₆CH(OH)R₈ affords carbamate 1-e, which is oxidized to 1-f by standard oxidation conditions. Preferred methods for the oxidation of secondary alcohols to the corresponding ketones include, but are not limited to, Dess-Martin periodinane (D. B. Dess et al. *J. Am. Chem. Soc.* 1991, 113, 7277 and *J. Org. Chem.* 1983, 48, 4155), Swern oxidation as well as its variations (D. Swern et al. *J. Org. Chem.* 1978, 43, 2480; T. T. Tidwell *Org. React.* 1990, 39, 297; M. Hudlicky *Oxidations in Organic Chemistry*; ACS: Washington, 1990), PCC (E. J. Corey et al. *Tetrahedron Lett.* 1975, 2647; G. Piancatelli *Synthesis* 1982, 245), PDC (E. J. Corey et al. *Tetrahedron Lett.* 1979, 399) and TPAP catalyzed oxidation (S. V. Ley et al. *Synthesis* 1994, 639).

oxidation of alcohols to the corresponding aldehydes include, but are not limited to, Dess-Martin periodinane (D. B. Dess et al. *J. Am. Chem. Soc.* 1991, 113, 7277 and *J. Org. Chem.* 1983, 48, 4155), Swern oxidation as well as its variations (D. Swern et al. *J. Org. Chem.* 1978, 43, 2480; T. T. Tidwell Org. React. 1990, 39, 297; M. Hudlicky *Oxidations in Organic Chemistry*; ACS: Washington, 1990), TEMPO/trichloroisocyanuric acid (L. De Luca et al. *Org. Lett.* 2001, 3, 3041) and TPAP catalyzed oxidation (S. V. Ley et al. *Synthesis* 1994, 639). Addition of the Grignard reagent derived from benzoxazole to 2-c provides the 2-d, which is de-protected to yield the amino alcohol 2-e.

The preferred synthesis for substituted benzoxazoles used in this invention that are not commercially available is the cyclo-condensation of o-aminophenyl with trimethyl orthoformate. For references, see A. R. Katritzky et al. *Heterocycles* 1995, 41, 345; J. H. Musser et al. *J. Med. Chem* 1985, 28, 1255; and K. R. Kunz et al. *OPPI* 1990, 22, 613.

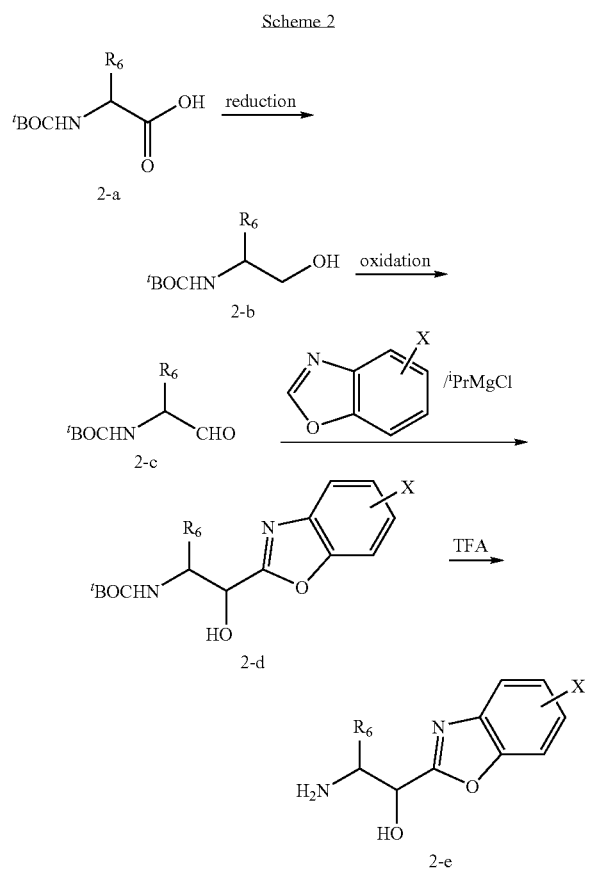

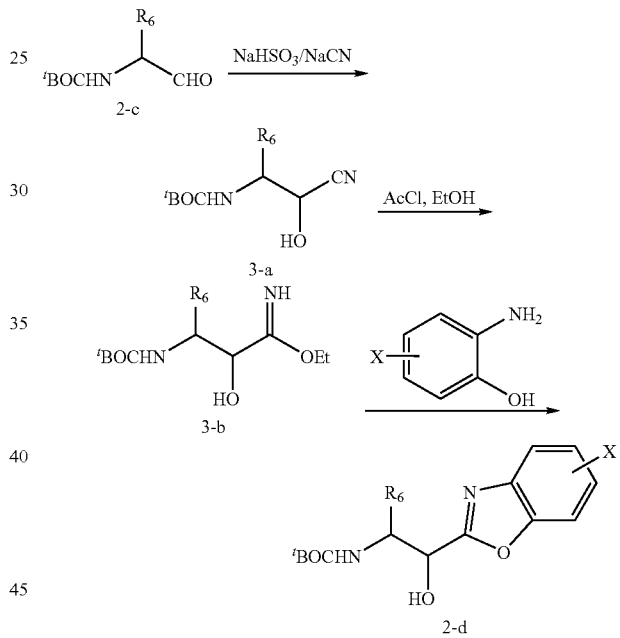

The preparation of the vicinal amino alcohol NH₂CHR₆CH(OH)R₈, wherein R⁸ is an benzoxazole optionally substituted with 0-3 X, wherein X is the substitutents of R₈ as defined in claim 1, is exemplified in Scheme 2. A N-protected amino acid is reduced using either the BH₃ method or NaBH₄ reduction of its mixed anhydride with isobutyl chloroformate [see R. C. Larock *A guide to functional group preparations* pp. 548-552, Wiley-V C H, 1989] to obtain 2-b (Scheme 2). One can then oxidize the resulting alcohol 2-b to the aldehyde 2-c. Preferred methods for the Alternatively, amino alcohol 2-d can be made by the reaction sequence described in Scheme 3 (see M. E. McGrath et al. *Biochemistry* 2003, 42, 15018). Amino aldehyde 2-c is converted to cyanohydrin 3-a (C. H. Heathcock et al. *Org. Synth.* Coll. Vol. 7, p 381), which is then treated with anhydrous ethanol and acetyl chloride to provide imidate ester 3-b. The condensation of 3-b with o-aminophenol affords the amino alcohol 2-d.

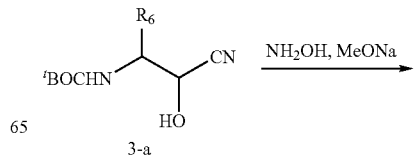

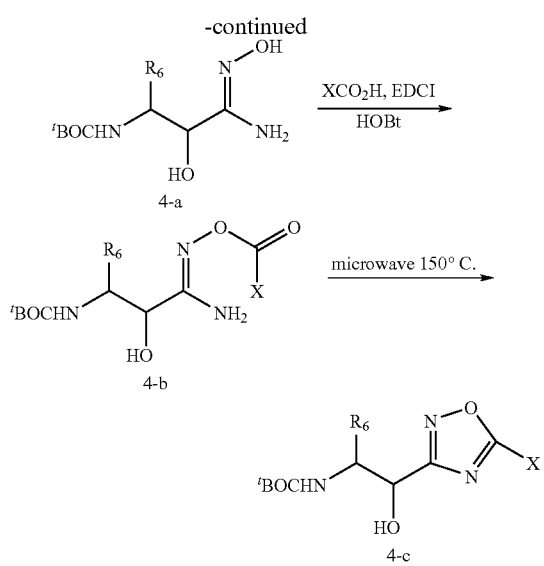

The preparation of the vicinal amino alcohol 'BOCNHCHR$_6$CH(OH)R$_8$, wherein R$^8$ is an 1,2,4-oxadiazole optionally substituted with 0-1 X, wherein X is the substituents of R$_8$ as defined in claim 1, is exemplified in Scheme 4. Hydroxylamine is added to the cyanohydrin 3-a under basic condition to form hydroxy amidine 4-a, which is acylated with XCOOH (or its corresponding acyl chloride or anhydride) to afford 4-b. 4-b is heated under microwave to cyclize to oxadiazole 4-c.

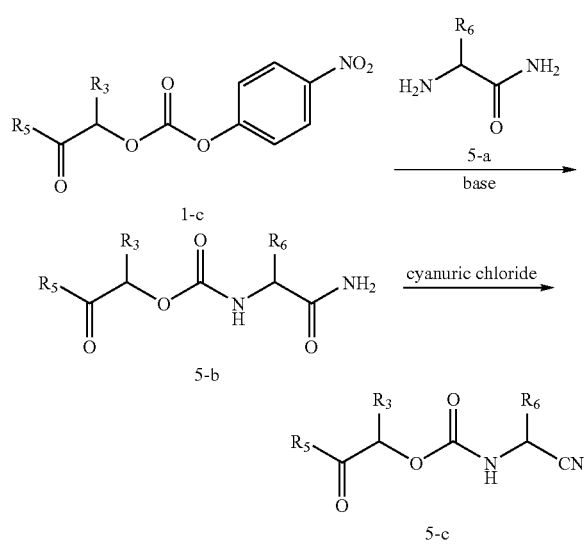

An illustration of the synthesis of the compounds in the present invention in which R$_1$ is —CHR$_6$CN, and R$_2$ and R$_4$ are both hydrogen is given in Scheme 5. α-Amino amide 5-a is added to the mixed carbonate 1-c. The product 5-b is dehydrated with cyanuric chloride to provide 5-c. For detailed discussions on the preparation of non-commercially available α-amino amides and their conversions to the corresponding α-amino nitrites, see Y. D. Ward et al. *J. Med. Chem.* 2002, 45, 5471; P. D. Greenspan et al. *J. Med. Chem.* 2001, 44, 4524. Additional Processes for Making Compounds of the Invention A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base. Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", 3$^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxane, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, the compounds of Formula I can be made by a process, which involves:
(a) that of reaction schemes 1, 2, 3, 4 or 5; and
(b) optionally converting a compound of the invention into a pharmaceutically acceptable salt;
(c) optionally converting a salt form of a compound of the invention to a non-salt form;
(d) optionally converting an unoxidized form of a compound of the invention into a pharmaceutically acceptable N-oxide;
(e) optionally converting an N-oxide form of a compound of the invention to its unoxidized form;
(f) optionally resolving an individual isomer of a compound of the invention from a mixture of isomers;
(g) optionally converting a non-derivatized compound of the invention into a pharmaceutically acceptable prodrug derivative; and
(h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The present invention is further exemplified, but not limited, by the following examples that illustrate the preparation intermediates (reference 1) and of compounds of the invention (Examples).

Reference 1

Preparation of c-h droxy Acid Via Diazotization of Chiral Amino Acid (Representative Procedure)

To a stirring suspension of L-cyclohexylalanine (4.00 g, 23.4 mmol) in 0.5M $H_2SO_4$ (120 mL) at 0° C. is slowly added dropwise an aqueous solution of $NaNO_2$ (12.1 g in 40 mL $H_2O$). Addition is complete after approximately 1 hour, at which point the solution is allowed to warm to room temperature. After 16 hours, the reaction mixture is extracted with ether (3×100 mL), and the combined organic extracts are washed with 1M $NaHSO_4$ (1×200 mL) and brine (1×100 mL) and then dried over anhydrous $Na_2SO_4$. The solvent is removed in vacuo, and the crude product is recrystallized from $Et_2O$/pentane (10 mL/100 mL) to afford 2.1 g (52% yield) of (S)-2-hydroxy-3-cyclohexylpropionic acid as fine white needles.

Example 1

2-cyclohexyl-(1S)-(morpholine-4-carbonyl)ethyl 2-(benzooxazol-2-yl)-(1S)-cyclopropyl-2-oxo-ethyl carbamate

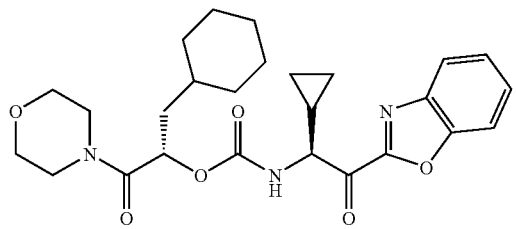

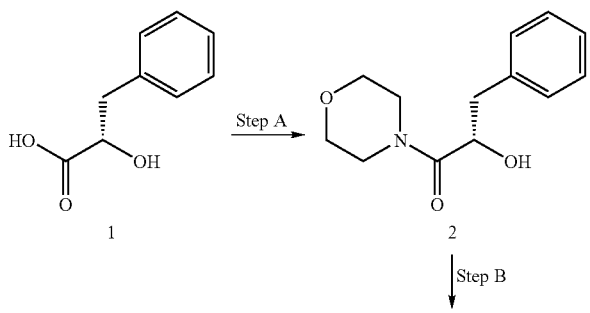

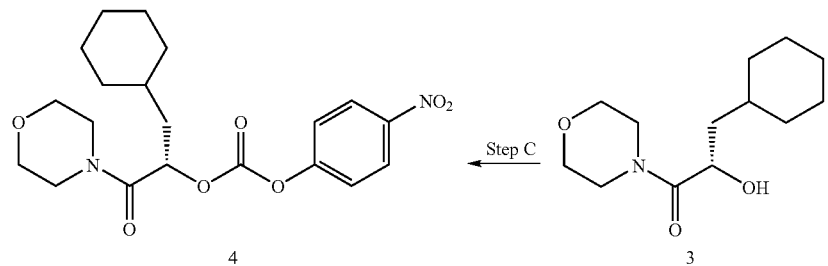

Step A: A sample of (S)-3-phenyllactic acid (1, 21 g, 126 mmol) is dissolved in dichloromethane (300 mL) and treated with morpholine (55 g, 631 mmol). The reaction is cooled in an ice/water bath and a solution of PyBOP (72 g, 139 mmol) in dichloromethane (200 mL) is added dropwise through a pressure equalizing funnel. The reaction mixture is stirred overnight and allowed to warm to room temperature. After addition of 110 mL of 4 M HCl, the reaction mixture is filtered and the organics are separated. The aqueous layer is extracted twice with dichloromethane and discarded. The combined organics are dried over $MgSO_4$ and the solvent is removed. The resulting material is chromatographed on silica gel and eluted with ethyl acetate to afford 20.65 g (68% yield) of (S)-2-hydroxy-1-morpholin-4-yl-3-phenyl-propan-1-one (2) as an oil; HPLC-MS calculated for $C_{13}H_{17}NO_3$ (M+H$^+$) 236.1, found 236.4.

Step B: A solution of 2 (20.5 g, 87.1 mmol) in a mixture of ethanol (80 mL), water (10 mL) and acetic acid (10 mL) is charged to a Parr bomb and treated with 2 g of 10% Rh/C. The bomb is sealed, evacuated and pressurized to 1000 psi with hydrogen. The reaction is then heated to 50° C. with stirring overnight. After cooling to room temperature and relieving the pressure, the bomb is evacuated and back filled with nitrogen twice. The reaction mixture is filtered through a pad of celite and the solvent is removed to afford 18.6 g (88.5%) of (S)-3-cyclohexyl-2-hydroxy-1-morpholin-4-yl-propan-1-one (3) as an oil; HPLC-MS calculated for $C_{13}H_{23}NO_3$ (M+H$^+$) 242.2, found 242.4.

Step C. A solution of 4-nitrophenyl chloroformate (20.55 g, 102 mmol) in dioxane (150 mL) is treated with pyridine (50 mL) resulting in a suspension. This material is heated to 70° C. and a solution of 3 (12.30 g, 51.0 mmol) in dioxane (50 mL) is added via pressure equalizing dropping funnel over 5 minutes. After stirring for an additional 5 minutes, the reaction is allowed to cool to room temperature and the solvent is removed by rotary evaporation. The resulting mass is partitioned between ethyl acetate and water. The organic layer is collected and the aqueous phase is extracted once more with ethyl acetate and discarded. The combined organics are dried over $MgSO_4$ and the solvent is removed. The resulting solid is dissolved in a minimal amount of hot dichloroethane and treated with dichloromethane. The mixture is then kept in a –4° C. refrigerator overnight and filtered. The mother liquor is concentrated and purified over 330 g of silica gel using a gradient of 0-100% ethyl acetate in hexane to afford 15.2 g (73% yield) of (S)-2-cyclohexyl-1-(morpholine-4-carbonyl) ethyl 4-nitro-phenyl carbonate (4) as a slightly yellow oil; $^1$H NMR (CDCl$_3$, 400 MHz) δ 0.97-1.08 (m, 2H), 1.09-1.36 (m, 3H), 1.48-4.62 (m, 2H), 1.65-1.68 (m, 4H), 1.82-1.97 (m, 2H), 3.41-3.60 (m, 3H), 3.64-3.80 (m, 5H), 5.29-5.36 (m, 1H), 7.38-7.44 (m, 2H), 8.24-8.30 (m, 2H); HPLC-MS calculated for $C_{20}H_{26}N_2O_7$ (M+H$^+$) 407.2, found 407.4.

Scheme 7

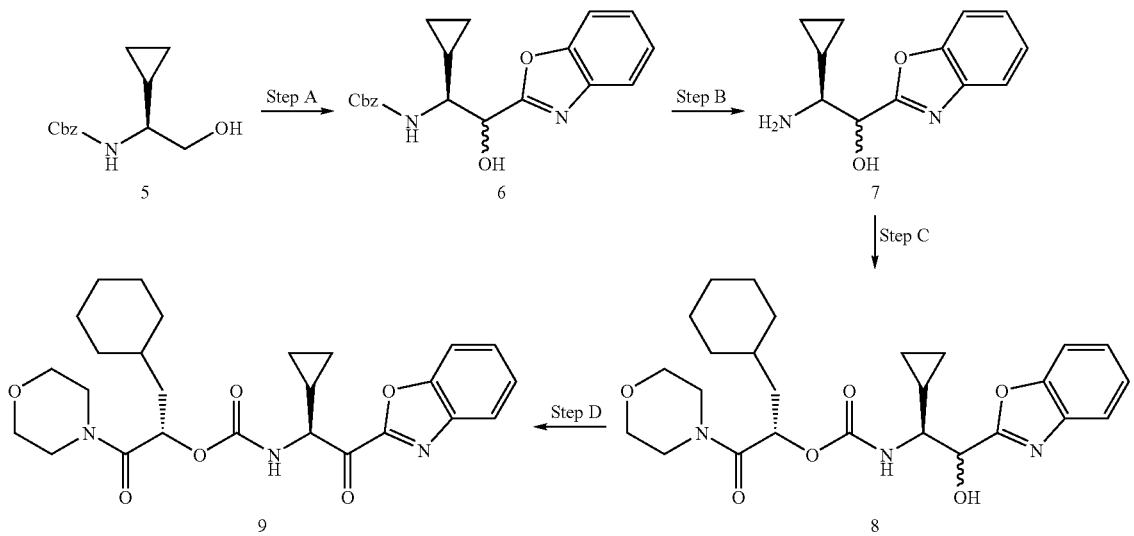

(S)-(1-cyclopropyl-2-hydroxy-ethyl)-carbamic acid benzyl ester (5) used in Scheme 7 is prepared as follows:

(i) A sample of (S)-phenethyl-(S)-cyclopropyl glycine (16.8 g, 76.7 mmol, prepared from cyclopropanecarboxaldehyde, potassium cyanide and (S)-(−)-α-methylbenzylamine using a modified procedure reported in Daniel J. Bayson et al. U.S. Pat. No. 6,191,306) is treated with THF (200 mL), water (100 mL) and 10% Pd/C (4.76 g). To the stirring mixture is added formic acid (17 mL) and the reaction mixture is stirred overnight. The catalyst is then removed by filtration through a pad of Celite and the solvent is removed by rotary evaporation. The material is coevaporated with methanol several times and dried under vacuum to afford 4.75 g (54% yield) of (S)-amino-cyclopropyl-acetic acid as a solid which is used without further purification.

(ii) The material from the previous step (4.75 g, 41 mmol) is dissolved in 130 mL of 1 N NaOH and treated with benzyl chloroformate (5.92 g, 49.5 mmol) with vigorous stirring. The reaction is stirred overnight and then extracted with dichloromethane twice. The organics are discarded and the aqueous phase is acidified with conc. HCl and extracted with dichloromethane three times. The combined organics are dried over $MgSO_4$ and the solvent is removed to afford 7.38 g (72% yield) of (S)-benzyloxycarbonylamino-cyclopropyl-acetic acid as a white solid.

(iii) A solution of (S)-benzyloxycarbonylamino-cyclopropyl-acetic acid (3.2 g, 12.8 mmol) in THF (20 mL) is cooled in an ice/water bath and treated with a 1 M solution of BH$_3$ in THF (16.7 mL, 16.7 mmol). The reaction is stirred for 4 hours and then treated with 1 M HCl until the bubbling ceased. The mixture is stirred overnight and the organic solvent is removed by rotary evaporation. The residue is treated with ethyl acetate and transferred to a separatory funnel. The aqueous phase is discarded and the organics are washed twice with 1 M NaOH, dried over MgSO$_4$ and the solvent is removed. The residue is purified on silica gel using a gradient of 0-100% ethyl acetate in hexane to afford 1.5 g (50% yield) of the alcohol as a white solid; $^1$H NMR (CDCl$_3$, 400 MHz) δ 0.26-0.37 (m, 1H), 0.34-0.44 (m, 1H), 0.47-0.61 (m, 2H), 0.83-0.94 (m, 1H), 2.95-3.04 (m, 1H), 3.70 (dd, 1H, J$_1$=5.8, J$_2$=11.1), 3.79-3.88 (m, 1H), 5.00-5.12 (m, 1H), 5.10 (s, 2H), 7.29-7.31 (m, 5H); HPLC-MS calculated for C$_{13}$H$_{17}$NO$_3$ (M+H$^+$) 236.1, found 236.3.

Synthesis of 2-cyclohexyl-(1S)-(morpholine-4-carbonyl) ethyl 2-(benzoxazol-2-yl)-(1S)-cyclopropyl-2-oxo-ethyl carbamate (Scheme 7).

Step A. This transformation is performed according to the procedures described in M. Graupe et al. WO 02098850, Reference Example 17(a) except that Dess-Martin periodinane is used to convert 5 to its corresponding aldehyde, to provide 1-(S)-cyclopropyl-2-(benzoxazol-2-yl)-2-hydroxyethyl]-carbamic acid benzyl ester (6) in 45% overall yield; HPLC-MS calculated for C$_{20}$H$_{20}$N$_2$O$_4$ (M+H$^+$) 353.1, found 353.4.

Step B, C and D. A solution of 6 (269 mg, 0.763 mmol) in methanol (8 mL) is treated with 20% Pd(OH)$_2$ on carbon (34 mg). The atmosphere in the reaction is exchanged for hydrogen by sparging the solution with a long needle for 3 minutes and the reaction is stirred under 1 atmosphere of hydrogen for 2 hours. The atmosphere is exchanged back to nitrogen by again sparging the solution with a long needle for 3 minutes. The reaction is filtered through Celite and the solvent is removed. The resulting oil is treated with a solution of 4 (310 mg, 0.763 mmol) in ethyl acetate and the solvent is removed. The mixture is then dissolved in isopropyl alcohol (10 mL) and treated with diisopropylethylamine (148 mg, 1.15 mmol). The reaction is then heated to 50° C. overnight. The volatiles are removed in vacuo and the remaining residue is dissolved in ethyl acetate and washed with 5% NaHSO$_4$ solution. The organics are dried over MgSO$_4$ and the solvent is removed. The resulting oil is dissolved in dichloromethane (10 mL) and treated with Dess-Martin periodinane (937 mg, 2.21 mmol). After stirring overnight, the reaction is treated with saturated aqueous NaHCO$_3$ (~15 mL) and 1 M Na$_2$S$_2$O$_3$ (~15 mL) and stirred for 20 minutes. The mixture is then transferred to a separator funnel and the organic layer is collected. The aqueous layer is extracted twice with dichloromethane and discarded. The combined organics are dried over MgSO$_4$ and the solvent is removed. The residue is purified over silica gel using a gradient of 0 to 100% ethyl acetate in hexane to afford 114 mg (31% yield) of 2-cyclohexyl-(1S)-(morpholine-4-carbonyl)ethyl 2-(benzooxazol-2-yl)-(1S)-cyclopropyl-2-oxo-ethyl carbamate as a solid after lyophilisation; $^1$H NMR (CDCl$_3$, 400 MHz) δ 0.51-0.65 (m, 3H), 0.73-1.00 (m, 3H), 1.04-1.29 (m, 4H), 1.35-1.47 (m, 2H), 1.58-1.84 (m, 6H), 3.37-3.76 (m, 8H), 4.88-4.93 (m, 1H), 5.29 (dd, 1H, J$_1$=2.7, J$_2$=10.1), 5.82 (d, 1H, J=7.1), 7.44-7.50 (m, 1H), 7.52-7.58 (m, 1H), 7.67(d, 1H, J=8.3), 7.90 (d, 1H, J=8.0); HPLC-MS calculated for C$_{26}$H$_{33}$N$_3$O$_6$ (M+H$^+$) 484.2, found 484.5.

Example 2

2-phenylmethanesulfonyl-(1R)-(morpholine-4-carbonyl)ethyl 2-(benzoxazol-2-yl)-(1S)-methyl-2-oxo-ethyl carbamate

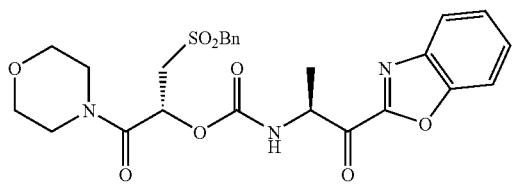

Scheme 8

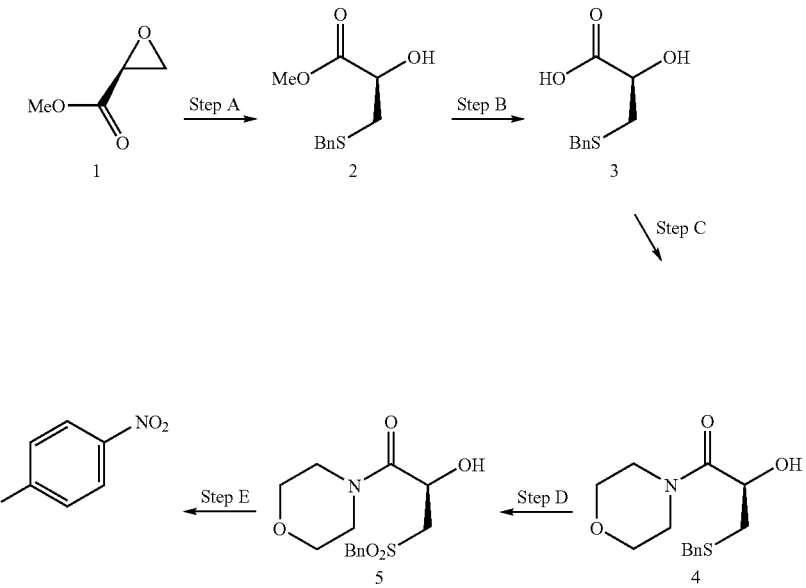

Step A: This reaction is performed as previously described by Deechongkit, S.; You, S.-L.; Kelly, J. W. *Org. Lett.* 2004, 6, 497, using (S)-Methylglycidate 1 and benzyl mercaptan. (R)-3-benzylsulfanyl-2-hydroxy-propionic acid methyl ester 2 (7.41 g, mmol, 31.41 mmol, 92%) is isolated as a viscous oil: MS calculated for $C_{11}H_{14}O_3S$ (M+H$^+$) 227.1, found 227.3.

Step B: This reaction is performed as previously described by Deechongkit, S.; You, S.-L.; Kelly, J. W. *Org. Lett.* 2004, 6, 497, using (R)-3-benzylsulfanyl-2-hydroxy-propionic acid methyl ester 2 and lithium hydroxide. (R)-3-Benzylsulfanyl-2-hydroxy-propionic acid 3 (3.08 g, 14.51 mmol, 46%) is isolated as a viscous oil: MS calculated for $C_{10}H_{12}O_3S$ (M+Na$^+$) 235.1, found 235.3.

Step C: This reaction is performed as previously described in Example 1, using (R)-3-benzylsulfanyl-2-hydroxy-propionic acid 3. (R)-3-Benzylsulfanyl-2-hydroxy-1-morpholin-4-yl-propan-1-one 4 (3.41 g, 11.87 mmol, 67%) is isolated as a viscous oil: MS calculated for $C_{14}H_{19}NO_3S$ (M+H$^+$) 282.1, found 282.4.

Step D: Oxone (2KHSO$_5$.KHSO$_4$.K$_2$SO$_4$, 10.55 g, 17.17 mmol, 3.0 eq.) is dissolved in H$_2$O (25 mL, 0.7 M) and added to a MeOH (25 mL, 0.3 M) solution of (R)-3-Benzylsulfanyl-2-hydroxy-1-morpholin-4-yl-propan-1-one 4 (1.61 g, 5.73 mmol, 1.0 eq.) at 0° C. over a 30 minutes period. The reaction is monitored to completion by LC/MS. After the reaction is judged to be complete (about 12 hours), the MeOH is evaporated in vacuo. The resulting solution is diluted with H$_2$O (30 mL) and extracted with CH$_2$Cl$_2$ (3×50 mL). The organic extracts are combined, washed with H$_2$O (75 mL) and saturated NaCl (50 mL). The organic layer is dried over MgSO$_4$ and filtered. The organic solvent is removed in vacuo and provided (R)-2-hydroxy-1-morpholin-4-yl-3-phenylmethanesulfonyl-propan-1-one (5) as a viscous oil (1.60 g, 5.11 mmol, 89%) which is used directly without further purification: MS calculated for $C_{14}H_{19}NO_5S$ (M+H$^+$) 314.1, found 314.3.

Step E: This reaction is performed as previously described in Example 1, using (R)-2-Hydroxy-1-morpholin-4-yl-3-phenylmethanesulfonyl-propan-1-one 5. (R)-1-(morpholine-4-carbonyl)-2-phenylmethanesulfonyl-ethyl 4-nitrophenyl carbonate 6 (1.98 g, 4.14 mmol, 81%) is isolated as a white solid after column chromatography: MS calculated for $C_{21}H_{22}N_2O_9S$ (M+H$^+$) 479.1, found 479.3.

This material is then used to synthesize the title compound using a procedure analogous to those described in Example 1; $^1$H NMR (CD$_3$OD, 600 MHz) δ 1.54 (d, 3H, J=6.6 Hz), 3.51-3.69 (m, 10H), 4.51-4.58 (m, 2H), 5.08-5.10 (m, 1H), 5.74-5.77 (m, 1H), 6.94-7.01 (m, 1H), 7.28-7.58 (m, 6H), 7.72-7.79 (m, 1H), 7.93 (d, 1H, J=8.4 Hz); HPLC-MS calculated for $C_{25}H_{27}N_3O_8S$ (M+H$^+$) 530.2, found 530.4.

Example 3

2-cyclohexyl-(1S)-(morpholine-4-carbonyl)ethyl (1S)-(5-ethyl-[1,2,4]oxadiazole-3-carbonyl)propyl carbamate

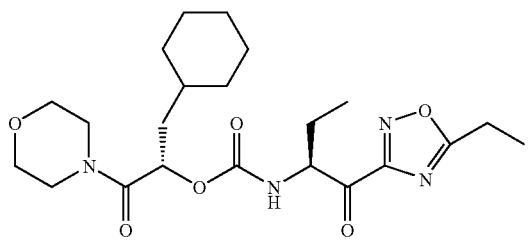

This material is prepared in 49% yield by using (S)-2-amino-1-(5-ethyl-1,2,4-oxadiazol-3-yl)-butan-1-ol and (S)-2-cyclohexyl-1-(morpholine-4-carbonyl)ethyl 4-nitro-phenyl carbonate as described in Example 1. $^1$H NMR (CDCl$_3$, 400 MHz) δ 0.78-0.93 (m, 2H), 0.97 (dd, 3H, J$_1$=J$_2$=7.4), 1.05-1.30 (m, 3H), 1.33-1.44 (m, 1H), 1.43 (dd, 3H, J$_1$=J$_2$=7.6), 1.60-1.83 (m, 8H), 1.98-2.11 (m, 1H), 3.00 (q, 2H, J=7.6), 3.38-3.48(m, 1H), 3.50-3.58 (m, 2H), 3.60-3.76 (m, 5H), 5.18 (dd, 1H, J$_1$=4.8, J$_2$=7.8, J$_3$=12.6), 5.26-5.32 (m, 1H), 5.67 (d, 1H, J=8.2); HPLC-MS calculated for $C_{22}H_{34}N_4O_6$ (M+H$^+$) 451.3, found 451.5.

Example 4

2-cyclohexyl-(1S)-(morpholine-4-carbonyl)ethyl (1S)-(5-phenyl-[1,2,4]oxadiazole-3-carbonyl)propyl carbamate

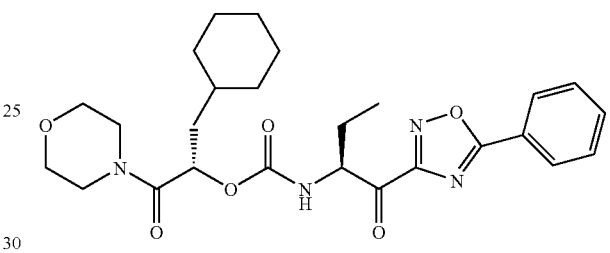

This material is prepared in 49% yield using (S)-2-amino-1-(5-phenyl-1,2,4-oxadiazol-3-yl)-butan-1-ol and (S)-2-cyclohexyl-1-(morpholine-4-carbonyl)ethyl 4-nitro-phenyl carbonate as described in Example 1. $^1$H NMR (CDCl$_3$, 400 MHz) δ 0.80-1.03 (m, 2H), 1.01 (dd, 3H, J$_1$=J$_2$=7.4), 1.06-1.32 (m, 2H), 1.39-1.89 (m, 9H), 2.04-2.17 (m, 1H), 3.39-3.78 (m, 8H), 5.27 (ddd, 1H, J$_1$=4.9, J$_2$=7.7, J$_3$=12.6), 5.29-5.34 (m, 1H), 5.68 (d, 1H, J=8.2), 7.54-7.60 (m, 2H), 7.62-7.68 (m, 1H), 8.18-8.24 (m, 2H); HPLC-MS calculated for $C_{26}H_{34}N_4O_6$ (M+H+) 499.3, found 499.4.

Example 5

2-cyclohexyl-(1S)-(morpholine-4-carbonyl)ethyl 4-oxo-tetrahydro-furan-(3S)-yl carbamate

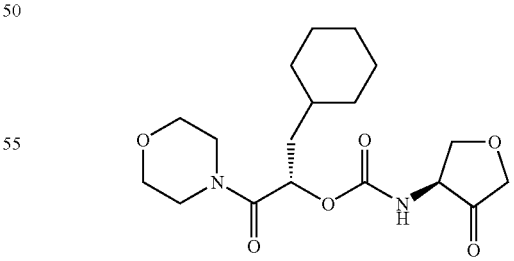

(4S)-Amino-tetrahydro-furan-(3R)-ol used is prepared as described by E. N. Jacobsen et al., *J. Am. Chem. Soc.*, 1995, 117, 5897-8.

2-cyclohexyl-(1S)-(morpholine-4-carbonyl)ethyl (4R)-hydroxyl-tetrahydro-furan-(3S)-yl carbamate is prepared as described in Example 1.

Scheme 9

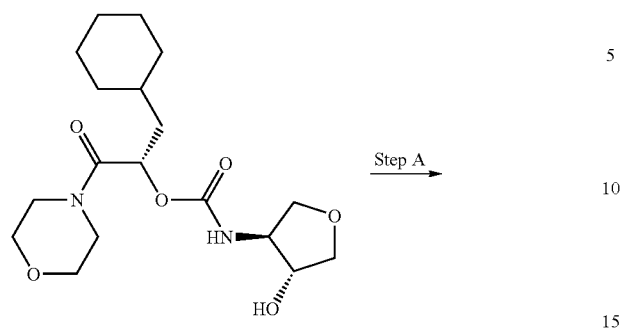

Scheme 10

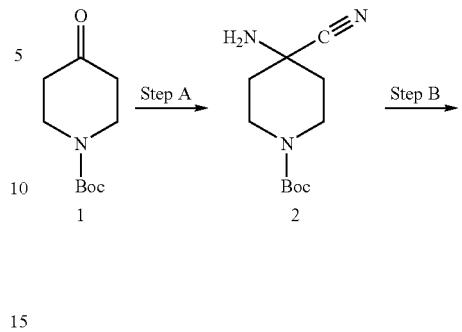

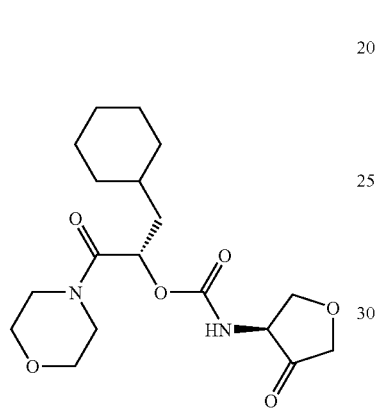

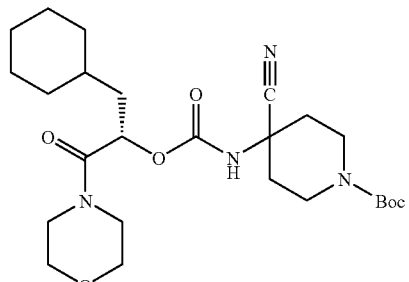

Step A: 2-cyclohexyl-(1S)-(morpholine-4-carbonyl)ethyl (4R)-hydroxyl-tetrahydro-furan-(3S)-yl carbamate (40 mg, 0.1079 mmol) is dissolved in dry dichloromethane (5 mL) and cooled to 0° C. Dess-Martin periodane is added as a solid and the reaction is allowed to stir at this temperature for half an hour before warming to room temperature over 1.5 hours. The volatiles are removed by rotary evaporation and the crude product purified by preparative HPLC yielding 15 mg, 37.5%. HPLC-MS calculated for $C_{18}H_{28}N_2O_6$ (M+H$^+$) 369.2, found 369.4.

Example 6

(S)-1-tert-Butoxycarbonal-4-cyano-4-(1-cyclohexyl-methyl-2-morpholin-4-yl-2-oxo-ethoxycarbony-lamino)-piperidine

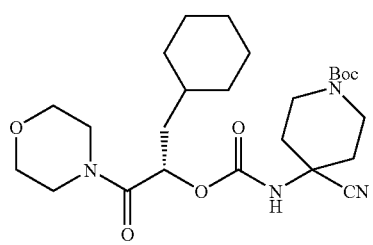

Step A: 1-Boc-4-piperidone 1 (2 g, 10 mmol) is added to a flask of KCN (3.256 g, 50 mmol) and ammonium acetate (7.7 g, 100 mmol). The flask is capped with a rubber septum and dry methanol (50 mL) is added via syringe. The reaction is sonicated for 15 minutes to break up the salts and then stirred at room temperature overnight. The volatiles are removed by rotary evaporation and the resulting residue is neutralized with saturated aqueous sodium bicarbonate solution and extracted with ethyl acetate. The organics are dried over MgSO$_4$ and the solvent is removed to afford 2.21 g, 98% yield of pure 4-amino-4-cyano-piperidine-1-carboxylic acid tert-butyl ester 2. $^1$H NMR (CDCl$_3$, 400 MHz) δ 3.95 (s, 2H), 3.18 (t, J=11.3 Hz, 2H), 1.96 (d, J=13.2 Hz, 2H), 1.82 (s, 2H), 1.63 (t, J=12 Hz, 2H), 1.45 (s, 9H).

Step B: A sample of 2 (192 mg, 0.852 mmol) and lutidine (91.3 mg, 0.852 mmol) are dissolved in dry DCM and added dropwise to a solution of triphosgene (278 mg, 2.81 mmol) in dry DCM. The reaction is allowed to stir for 1.5 hours at room temperature. (S)-3-cyclohexyl-2-hydroxy-1-morpholin-4-yl-propan-1-one (prepared as described in Example 1, 205 mg, 0.852 mmol) and lutidine (91.3 mg, 0.852 mmol) are added to the reaction as a solution in dry DCM dropwise over 10 minutes. The reaction is then stirred for 3 hours. The volatiles are removed in vacuo. The resulting residue is purified by preparative HPLC to afford 150 mg of (S)-1-tert-butoxycarbonyl-4-cyano-4-(1-cyclohexylmethyl-2-morpho-lin-4-yl-2-oxo-ethoxycarbonylamino)-piperidine. $^1$H NMR (CD$_3$OD, 400 MHz) δ 5.35 (d, J=9.2 Hz, 1H), 3.81 (d, J=10.5 Hz, 2H), 3.74-3.62 (m, 6H), 3.56-3.48 (m, 2H), 3.32 (m, 4H), 2.23 (d, J=11.2 Hz, 2H), 1.87 (m, 3H), 1.71 (m, 5H), 1.52-

1.46 (m, 11H), 1.29-1.20 (m, 3H), 1.03-0.97 (m, 2H). HPLC-MS calculated for $C_{25}H_{40}N_4O_6$ (M+H$^+$) 493.3, found 493.3.

Example 7

(S)-4-Cyano-4-(1-cyclohexylmethyl-2-morpholin-4-yl-2-oxo-ethoxycarbonylamino)-1-methyl-piperidine

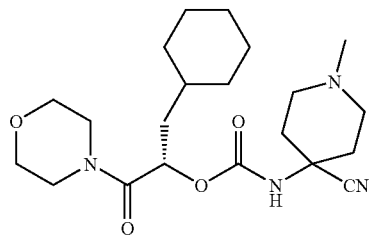

A sample of the title compound of Example 6 (125 mg, 0.254 mmol) is dissolved in DCM (1 mL) and TFA (1 mL). The reaction is allowed to stir for 1 hour and the volatiles are removed by rotary evaporation to afford pure (S)-4-cyano-4-(1-cyclohexylmethyl-2-morpholin-4-yl-2-oxo-ethoxycarbonylamino)-piperidine in quantitative yield as TFA salt. The corresponding free amine is prepared by addition of 1M NaOH and extraction into DCM followed by drying and rotary evaporation of the organic layer. HPLC-MS calculated for $C_{20}H_{32}N_4O_4$ (M+H$^+$) 393.2, found 393.3.

A sample of the free amine obtained from the previous step (40 mg, 0.102 mmol) is dissolved in MeOH (1 mL) and formaldehyde (6.06 mg, 0.202 mmol) is added as a solution in methanol (2 mL) with a single drop of acetic acid. Sodium cyanoborohydride (2.1 mg, 0.034 mmol) is added as a solid and the reaction is allowed to stir for half an hour. The solvent is removed in vacuo and the product is purified by preparative HPLC to afford the title material, 29.8 mg, 72% yield. HPLC-MS calculated for $C_{21}H_{34}N_4O_4$ (M+H$^+$)$_{407.3}$, found 407.3.

Example 8

(1S)-cyclohexylmethyl-2-morpholin-4-1-2-oxo-ethyl 2-(2-chloro-benzyloxy)-(1R)-cyano-ethyl carbamate Scheme 11

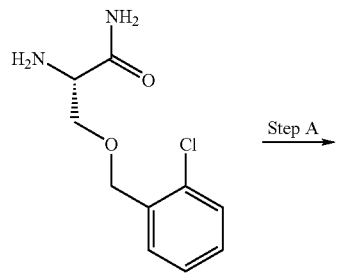

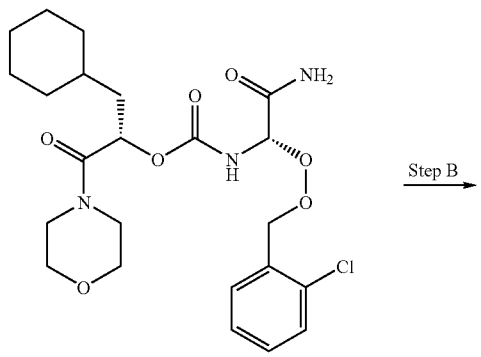

(S)-2-Amino-3-(2-chloro-benzyloxy)-propionamide is prepared as described by P. D. Greenspan et al., *J. Med. Chem.*, 2001, 44, 4524-4534.

Step A: (S)-2-cyclohexyl-1-(morpholine-4-carbonyl)ethyl 4-nitro-phenyl carbonate (prepared in Example 1, 132.8 mg, 0.326 mmol) and (S)-2-amino-3-(2-chloro-benzyloxy)-propionamide (89.7 mg, 0.392 mmol) are added to a dry flask with 2 mL of anhydrous DMF. DMAP (159 mg, 1.3 mmol) is added in 0.5 mL of dry DMF and the reaction mixture is stirred overnight. After workup, the product is obtained by preparative HPLC purification in 39% yield as an amorphous solid. HPLC-MS for $C_{24}H_{34}ClN_3O_6$ (M+1)=496.9.

Step B: The product of Step A (61 mg, 0.122 mmol) is dissolved in 0.5 mL of dry DMF and added to a solution of cyanuric chloride (67 mg, 0.369 mmol) in dry DMF. The reaction mixture is allowed to stir for 2 hours, and then the solvent is removed by rotary evaporation and the crude material is purified by preparative HPLC, yielding 14.66 mg of a pure amorphous solid. $^1$H NMR (CD$_3$OD, 400 MHz) δ 7.59 (d, J=7.1 Hz, 1H), 7.42 (d, J=7.3 Hz, 1H), 7.34 (m, 2H), 5.38 (d, J=9.8 Hz, 1H), 4.86 (t, J=5.7 Hz, 1H), 4.75 (d, J=1.8 Hz, 2H), 3.83 (d, J=5.6 Hz, 2H), 3.7-3.67(m, 6H), 3.6-3.49 (m, 2H), 1.87 (d, J=12.7 Hz, 1H), 1.77-1.72 (m, 5H), 1.58-1.49 (m, 2H), 1.37-1.18 (m, 3H), 1.09-0.92 (m, 2H). HPLC-MS for $C_{24}H_{32}ClN_3O_5$ (M+1)=479.2.

Example 45

2-cyclohexyl-(1S)-(morpholine-4-carbonyl)ethyl (1S)-(5-cyclopropyl-[1,2,4]oxadiazole-3-carbonyl)-propyl carbamate

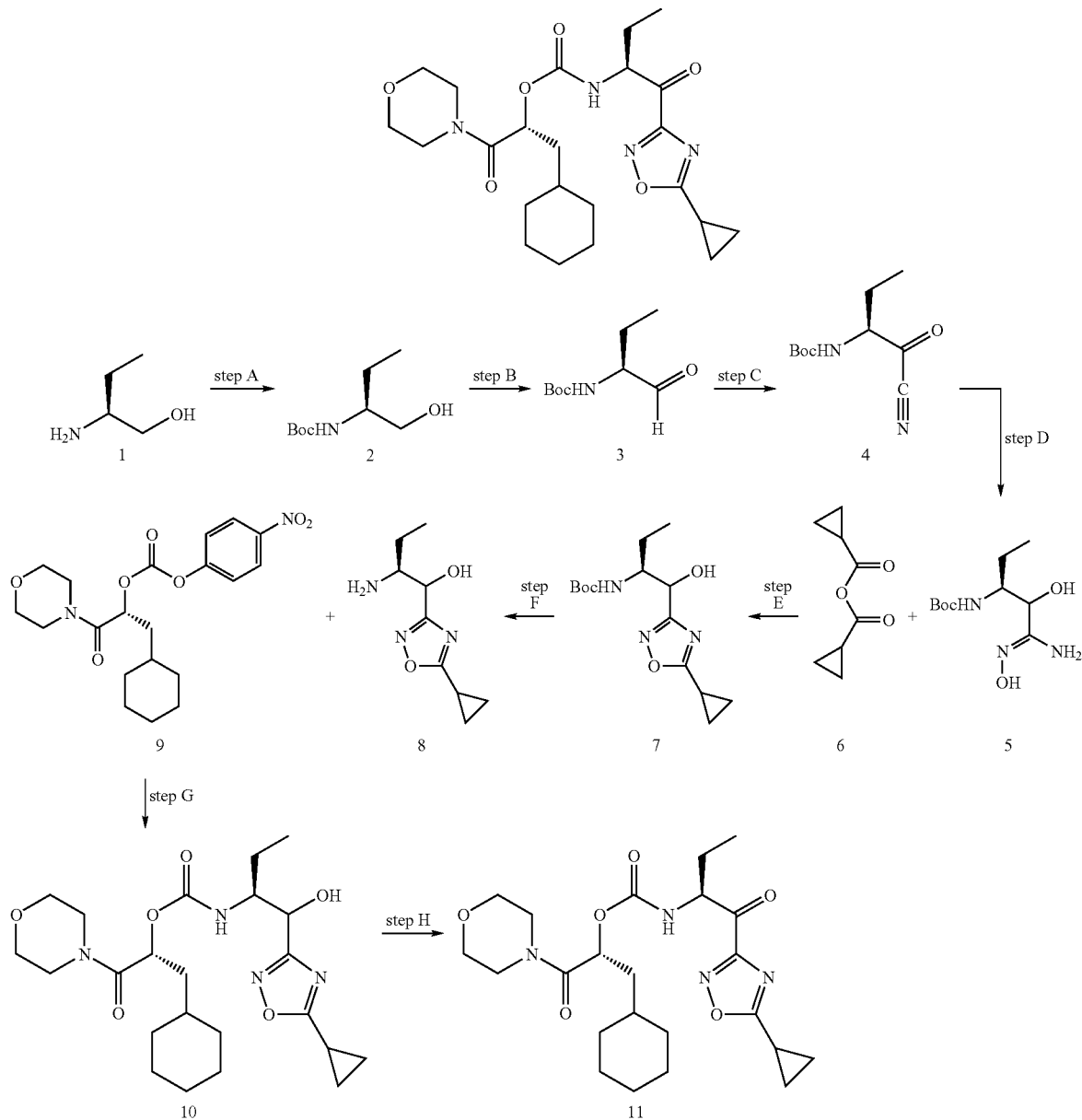

Step A: Intermediate 2 is synthesized from commercially available (S)-2-amino-butan-1-ol (1): 1 (10.0 g, 112 mmol, 1.0 eq) is dissolved in 500 mL of dry DCM. Boc anhydride (26.93 g, 123.4 mmol, 1.1 eq) is dissolved in 200 mL of dry DCM and added to 1 at 0° C. via addition funnel over a period of 1 hour. After the reaction mixture is stirred overnight, it is worked up with 25% NH₄OH. The organic layer is separated and dried over MgSO₄. Evaporation of the solvent provides pure 2 in quantitative yield.

Step B: 2 (1.02 g, 5.39 mmol, 1 eq) is dissolved in 60 mL of dry DCM and cooled to 0° C. Trichloroisocyanuric acid (1.32 g, 5.65 mmol, 1.05 eq) is added and mixed for 10 minutes resulting in a white slurry. TEMPO is added (8.8 mg, 0.056 mmol, 0.01 eq) to the chilled reaction mixture which immediately turns orange and additional precipitate is formed. The reaction vessel is removed from the cold bath and the mixture is stirred for additional 45 minutes. The reaction mixture is then filtered through a pad of celite, washed with 5% citric acid followed by saturated bicarbonate, dried over MgSO₄, filtered, and stripped to yield pure 3 (0.979 g, 97% yield) which was used immediately in step C.

Step C: 3 (0.99 g, 5.28 mmol, 1 eq) is dissolved in 20 mL of dioxane and chilled to 0° C. for 10 minutes, to which NaHSO₃ (2.75 g, 21.1 mmol, 4 eq, dissolved in 10 mL of water) is added. The reaction mixture is allowed to stir at 0° C. for 10 minutes and KCN (1.37 g, 21.1 mmol, 4 eq, in 10 mL of water) is added. The reaction mixture is stirred overnight. The reaction mixture is worked up by diluting with 150 mL ethyl acetate and washing the organic layer with three portions of saturated sodium bicarbonate. The organic layer is dried over sodium sulfate, filtered and concentrated to dryness to yield the pure cyanohydrin in quantitative yield.

Step D: 4 (5.68 g, 26.5 mmol, 1 eq) is dissolved in 60 mL ethanol and hydroxyl amine (50% w/v) in water (2.44 mLs, 39.7 mmol, 1.5 eq) was added to the solution. The mixture is heated to 60° C. for 2 hours. The volatiles were removed and the resulting white foam was placed under high vacuum for 18 hours, resulting in an amorphous white solid of pure 5 in quantitative yield.

Step E: 5 (9.7 g, 39.23 mmol, 1 eq) is dissolved in 50 mL of dry DMF and cyclopropane carboxylic acid anhydride (6.148 g, 39.23 mmol, 1 eq) is added with vigorous stirring. The resulting solution is divided into five 20 mL microwave vials equipped with stirrer bars. The vials are capped and each heated individually to 200° C. for 75 seconds. The contents are then combined and diluted with 250 mL of ethyl acetate and washed with water, bicarbonate and brine. The organic layer is dried over magnesium sulfate, filtered, and concentrated to dryness. The resulting oil was chromatographed on an ISCO silica column, 20 to 80% ethyl acetate hexane gradient over 40 minutes. Yield 8.2 grams (70% yield).

Step F&G: 7 (8 g, 26.9 mmol, 1 eq) is dissolved in 50 mL of DCM and 50 mL of TFA is added slowly over 15 minutes to the stirring solution. The reaction mixture is stirred for 2 hours and then stripped to dryness. The resulting viscous oil is dissolved in 40 mL of dry DMF, to which DIPEA (17.35 g, 134.5 mmol, 5 eq) is added followed by a solution of 9 in 40 mL dry DMF. The resulting yellow solution is stirred overnight. DMF is partially removed to ca. 35 mL by rotary evaporation and the residue is diluted with 500 mL of ethyl acetate, washed with 4×200 mL portions of 25% $Na_2CO_3$. The organic layer is washed with brine, concentrated to dryness and taken up in methanol. The resulting mixture is purified by large scale reverse phase prep HPLC and the fractions are combined, stripped to remove acetonitrile, and extracted with ethyl acetate. The ethyl acetate was dried over $MgSO_4$, filtered, and stripped to yield pure 10 (11.5 g, 24.7 mmol, 92% yield).

Step H: 10 (8.8 g, 18.94 mmol, 1 eq) is dissolved in 500 mL dry DCM and cooled to 0° C. Dess-Martin periodane (24.1 g, 56.8 mmol, 3 eq) is added as a solid at 0° C. and the reaction mixture is allowed to warm to room temperature. The reaction mixture is stirred overnight and worked up with saturated $NaS_2O_3$ (400 mL) followed by saturated sodium bicarbonate. The organic layer is dried over $MgSO_4$, filtered and concentrated to 40 mL. The slurry is filtered and the solution chromatographed on two ISCO 110 grams columns with a 0 to 100% ethyl acetate gradient in 30 minutes, the ethyl acetate is then held at 100% for 15 minutes to ensure all of the product moves off the column. BPLC indicates a mix between the hydrate, methyl ketal (the sample was made up in methanol) and the desired product. $^1H$ NMR is clean and consistent.

Preparation of 6: Cyclopropane carboxylic acid (29 g, 336.9 mmol, 1 eq) is dissolved in 500 mL of dry DCM. DCC (34.75 g, 168.5 mmol, 0.5 eq) is added to the solution at 0° C. as a solution in 100 mL DCM dropwise over 0.5 hour. The reaction mixture is allowed to warm to rt and stirred overnight. The resulting slurry is filtered through a pad of celite, stripped, and dissolved in 500 mL of hexane, filtered through an additional pad of celite to remove the remaining byproducts and stripped. The resulting oil was vacuum distilled to yield the pure anhydride.

By repeating the procedures described in the above examples, using appropriate starting materials, the following compounds of Formula I, as identified in Table 1, are obtained.

TABLE 1

| Compound Number | Structure | Physical Data $^1$H NMR 400 MHz ($CDCl_3$) and/or MS (m/z) |
|---|---|---|
| 9 | 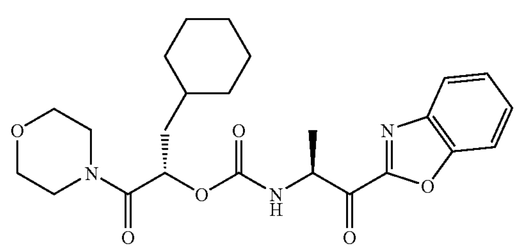 | $^1$HNMR ($CDCl_3$) δ(ppm) 7.84(m, 1H), 7.59(m, 1H) 7.48(m, 1H), 7.42(m, 1H), 5.70(m, 1H), 5.39(m, 1H), 5.26(m, 1H), 3.61(m, 5H), 3.49(m, 2H), 3.39(m, 1H), 1.70(m, 2H), 1.59(m, 4H), 1.54(d, J=7.6Hz, 3H), 1.37(m, 2H), 1.66(m, 3H), 0.91(m, 2H); HPLC-MS calculated for $C_{24}H_{31}N_3O_6$:458.2. found 458.5. |
| 10 | 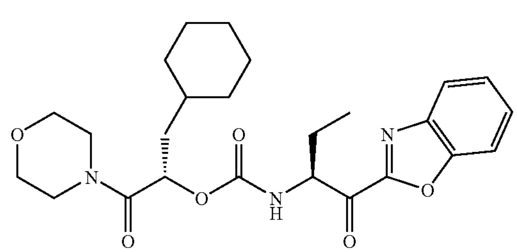 | $^1$HNMR($CD_3OD$, 400 MHz) δ 0.90-0.96(m, 2H), 1.09(t, 3H, J=7.2Hz), 1.19-1.29(m, 2H), 1.41-1.54 (m, 2H), 1.63-1.82(m, 8H), 2.08-2.17(m, 1H), 3.42-3.69(m, 8H), 5.18(dd, 1H, J=9.2, 4,4Hz), 5.29(dd, 1H, J=10.4, 3.2Hz), 7.51-7.54(m, 1H), 7.60-7.65(m, 1H), 7.72-7.77(m, 1H), 7.92(d, 1H, J=8.0Hz); HPLC-MS calculated for $C_{25}H_{33}N_3O_6$(M+H$^+$) 472.2, found 472.5, 433.9 |

TABLE 1-continued

| Compound Number | Structure | Physical Data $^1$H NMR 400 MHz (CDCl$_3$) and/or MS (m/z) |
|---|---|---|
| 11 | 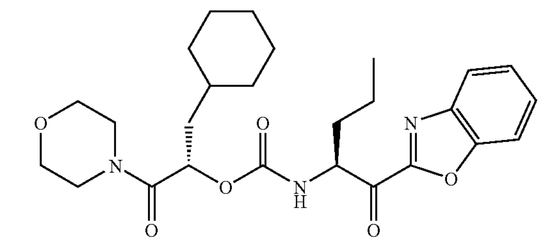 | $^1$HNMR(CD$_3$OD, 400MHz) δ 0.89-1.04(m, 5H), 1.19-1.29(m, 4H), 1.43-1.82(m, 10H), 2.08-2.17 (m, 1H), 3.44-3.70(m, 8H), 5.23 5.30(m, 2H), 7.53(dd, 1H, J= 8.0, 7.2Hz), 7.62(dd, 1H, J=8.0, 7.2Hz), 7.75(d, 1H, J=8.0Hz); HPLC-MS calculated for C$_{26}$H$_{35}$N$_3$O$_6$ (M+H$^+$) 486.3, found 486.5. |
| 12 | 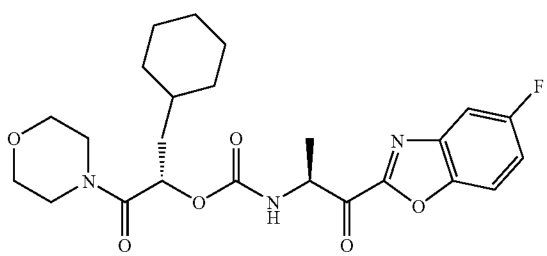 | $^1$HNMR(CDCl$_3$, 400MHz) δ 0.79-1.03(m, 2H), 1.06-1.33(m, 3H), 1.35-1.51(m, 2H), 1.61(d, 3H, J=7.3), 1.59-1.83(m, 6H), 3.35-3.78(m, 8H), 5.27-5.34(m, 1H), 5.38-5.58(m, 1H), 5.72(d, 1H, J=7.6), 7.30(ddd, 1H, J$_1$= 2.6, J$_2$=9.1, J$_3$=11.6), 7.57(dd, 1H, J$_1$=2.5, J$_2$=7.9), 7.59-7.64 (m, 1H); HPLC-MS calculated for C$_{24}$H$_{30}$FN$_3$O$_6$ $_{(M+H}$$^+$$_{)}$ 476.2, found 476.4 |
| 13 | 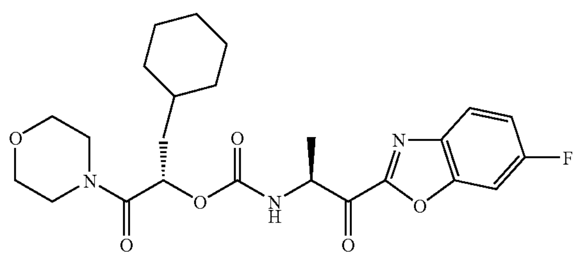 | $^1$HNMR(CDCl$_3$, 400MHz) δ 0.80-1.03(m, 2H), 1.06-1.30(m, 3H), 1.38-1.41(m, 2H), 1.60(d, 3H, J=7.3), 1.58-1.84(m, 9H), 3.39-3.76(m, 8H), 5.27-5.35(m, 1H), 5.38-5.48(m, 1H), 5.71(d, 1H, J=7.7), 7.23(dd, 1H, J$_1$=2.4, J$_2$=9.1), 7.37(dd, 1H, J$_1$=2.0, J$_2$=7.6), 7.87(dd, 1H, J$_1$=4.8, J$_2$= HPLC-MS calculated for C$_{24}$H$_{30}$FN$_3$O$_6$(M+H$^+$) 476.2, found 476.4 |
| 14 | 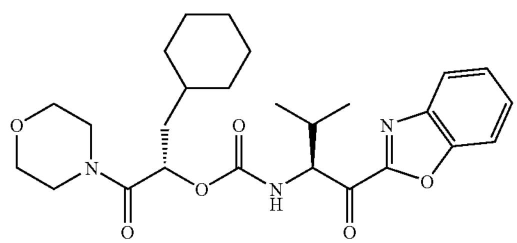 | $^1$HNMR(CD3OD, 400MHz) δ 0.89-1.03(m, 2H), 0.96(d, 3H), J= 6.8Hz), 1.06(d, 3H), J=6.8Hz), 1.13-1.29(m, 4H), 1.44-1.53(m, 2H), 1.66-1.80(m, 5H), 2.49 (quint, 1H, J=6.8Hz), 3.46-3.69 (m, 8H), 5.20(d, 1H, J=6.0Hz), 5.29(dd, 1H, J=10.4, 3.2Hz), 7.53(t, 1H, J=7.6Hz), 7.62(t, 1H, J=7.6Hz), 7.76(d, 1H, J= 8.4Hz), 7.93(1H, d, J=8.0Hz); HPLC-MS calculated for C$_{26}$H$_{35}$N$_3$O$_6$(M+ H+) 486.3, found 486.5 |
| 15 | 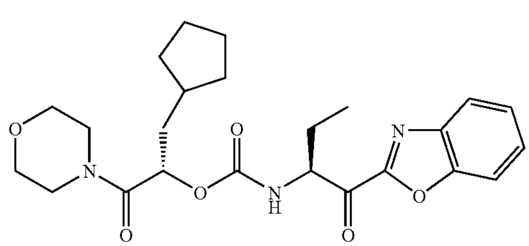 | $^1$HNMR(CDCl$_3$, 400MHz) δ1.02 (dd, 3H, J$_1$=J$_2$=7.4), 0.96-1.19 (m, 2H), 1.44-1.58(m, 2H), 1.44-1.58(m, 5H), 1.61-1.96(m, 5H), 2.09-2.12(m, 1H), 3.41-3.77(m, 8H), 5.26(dd, 1H, J$_1$= 4.1, J$_2$=8.9), 4.85-4.93(m, 1H), 5.78(d, 1H, J=8.3), 7.44-7.50(m, 1H), 7.51-7.58(m, 1H), 7.66(d, 1H, J=8.2), 7.90(d, 1H, J=8.0); HPLC-MS calculated for C$_{24}$H$_{31}$N$_3$O$_6$(M+H$^+$)458.2, fou |

TABLE 1-continued

| Compound Number | Structure | Physical Data $^1$H NMR 400 MHz (CDCl$_3$) and/or MS (m/z) |
|---|---|---|
| 16 | 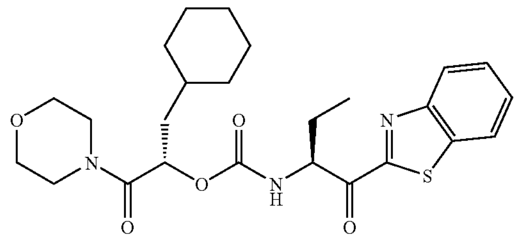 | $^1$HNMR(CD$_3$OD, 400MHz) δ 0.89-1.03(m, 2H), 1.08(t, 3H, J= 7.2 Hz), 1.16-1.29(m, 4H), 1.46-1.54(m, 2H), 1.64-1.85(m, 6H), 2.10-2.17(m, 1H), 3.47-3.71(m, 8H), 5.28-5.38(m, 2H), 7.60(dt, 1H, J=7.2, 1.2Hz), 7.64(dt, 1H, J=7.2, 1.2Hz), 8.11(d, 1H, J= 7.6Hz), 8.21(d, 1H), J=7.6Hz); HPLC-MS calculated for C$_{25}$H$_{33}$N$_3$O$_5$S (M+H$^+$) 488.2, found 488.4. |
| 17 | 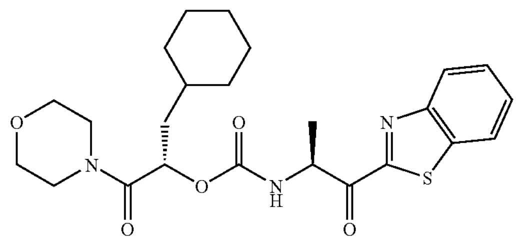 | HPLC-MS calculated for C$_{24}$H$_{31}$N$_3$O$_5$S(M+H$^+$) 474.2, found 474.4. |
| 18 | 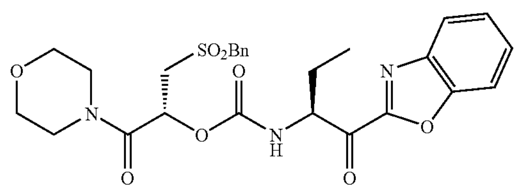 | HPLC-MS calculated for C$_{26}$H$_{29}$N$_3$O$_8$S(M+H$^+$) 544.2, found 544.4. |
| 19 | 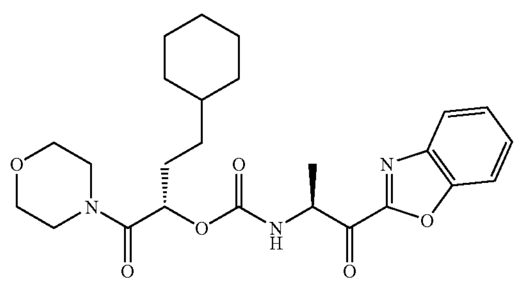 | $^1$HNMR(CD$_3$OD, 600MHz) δ 0.88-0.96(m, 2H, 1.16-1.39(m, 6H), 1.56(d, 3H), J=7.2Hz), 1.66-1.80(m, 7H), 3.49-3.71(m, 8H), 5.20(dd, 1H, J=7.8, 4.8Hz), 5.28 (q, 1H, J=7.2Hz), 7.54(t, 1H, J= 7.5Hz), 7.63(t, 1H, J=7.8Hz), 7.77(d, 1H, J=8.4Hz), 7.94(d, 1H, J=8.4Hz); HPLC-MS calculated for C$_{25}$H$_{33}$N$_3$O$_6$(M+H$^+$)472.2. |
| 20 | 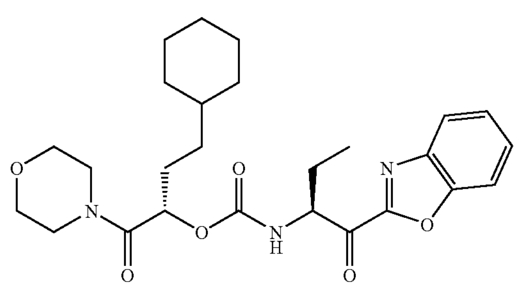 | HPLC-MS calculated for C$_{26}$H$_{25}$N$_3$O$_6$(M+H$^+$) 486.3, found 486.5. |
| 21 | 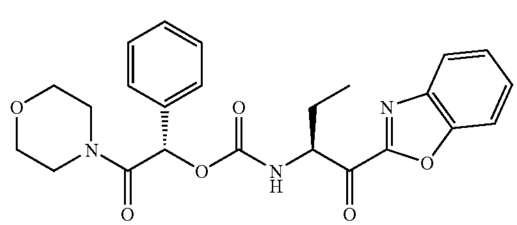 | HPLC-MS calculated for C$_{24}$H$_{25}$N$_3$O$_6$(M+H$^+$) 452.2, found 452.2. |

TABLE 1-continued

| Compound Number | Structure | Physical Data<br>¹H NMR 400 MHz (CDCl₃)<br>and/or MS (m/z) |
|---|---|---|
| 22 | 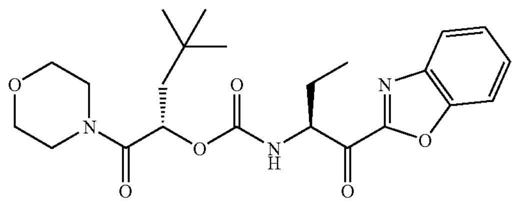 | ¹HNMR(CDCl³, 400MHz) δ0.96 (s, 9H), 1.03(dd, 3H, J₁=J₂= 7.4), 1.46-1.53(m, 1H), 1.83-1.92 (m, 2H), 2.10-2.23(m, 1H), 3.42-3.80 (m, 8H), 5.35-3.45(m, 2H), 5.70(d, 1H, J=8.1), 7.45-7.51(m, 1H), 7.53-7.59(m, 1H), 7.65-7.69 (m, 1H), 7.91(d, 1H, J=8.1); HPLC-MS calculated for C₂₃H₃₁N₃O₆(M+H⁺) 446.2, found 446.5 |
| 23 | 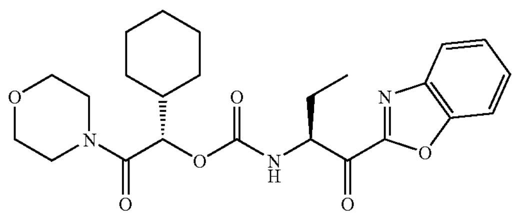 | HPLC-MS calculated for C24H31N3O6(M+H⁺) 458.2, found 458.4. |
| 24 | 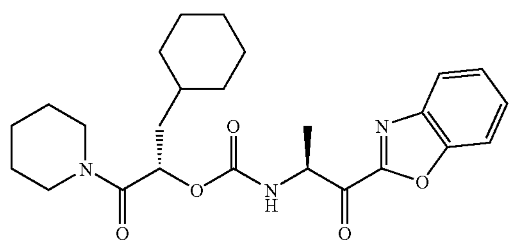 | C₂₅H₃₃N₃O₅; ¹HNMR(CDCl₃) δ(ppm) 7.84(m, 1H), 7.59(m, 1H), 7.49(m, 1H), 7.40(m, 1H), 5.65(d, 1H, J=5.1Hz, 1H), 5.41(m, 1H), 5.31(m, 1H), 3.53(m, 1H), 3.43(m, 1H), 3.40(m, 2H), 1.71(m, 2H), 1.58(m, 15H), 1.16(m, 3H), 0.89(m, 1H), 0.78(m, 1H); LCMS: 456.5(M+H)⁺. |
| 25 | 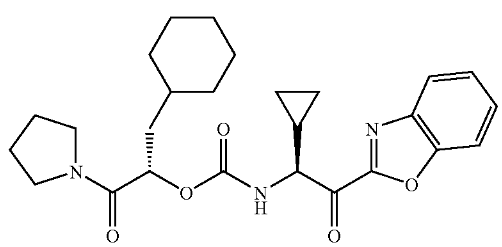 | C₂₆H₃₃N₃O₅; ¹HNMR(DMSO) δ(ppm) 8.25(m, 1H), 7.95(m, 1H), 7.86(m, 1H), 7.60(m, 1H), 7.49(m, 1H), 4.88(m, 1H), 4.44(m, 1H), 3.49(m, 1H), 3.18(m, 3H), 1.75(m, 2H), 1.64(m, 3H), 1.53(m, 5H), 1.30(m, 2H), 1.04(m, 4H), 0.84(m, 2H), 0.45(m, 4H); LCMS: 468.3(M+H)⁺. |
| 26 | 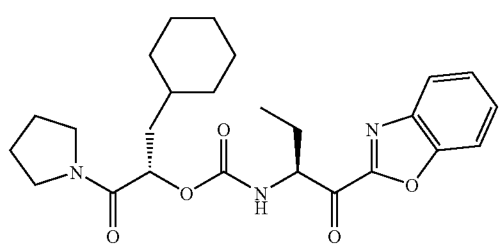 | C₂₅H₃₃N₃O₅; ¹HNMR(DMSO) δ(ppm) 8.00(m, 1H), 7.96(m, 1H), 7.85(m, 1H), 7.59(m, 1H), 7.50(m, 1H), 4.90(m, 2H), 3.37(m, 1H), 3.27(m, 5H), 3.19(m, 3H), 1.90(m, 1H), 1.76(m, 2H), 1.63(m, 3H), 1.54(m, 2H), 1.33(m, 2H), 1.06(m, 2H), 0.92(m, 3H), 0.77(m, 2H); LCMS 456.5(M+H)⁺. |
| 27 | 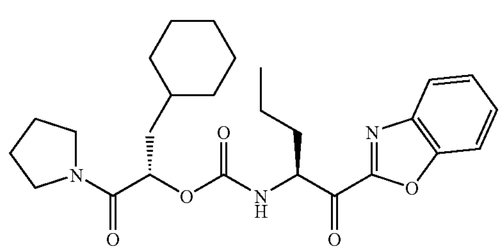 | ¹HNMR(DMSO) δ(ppm) 8.01(m, 1H), 7.96(m, 1H), 7.85(m, 1H), 7.96(m, 1H), 7.50(m, 1H), 5.2(m, 1H), 4.89(m, 1H), 3.33(m, 1H), 3.19(m, 3H), 1.76(m, 3H), 1.65(m, 3H), 1.58(m, 6H), 1.33(m, 4H), 1.06(m, 3H), 0.83(m, 5H); LCMS: 470.3(M+H)⁺. |

TABLE 1-continued

| Compound Number | Structure | Physical Data<br>$^1$H NMR 400 MHz (CDCl$_3$)<br>and/or MS (m/z) |
|---|---|---|
| 28 | 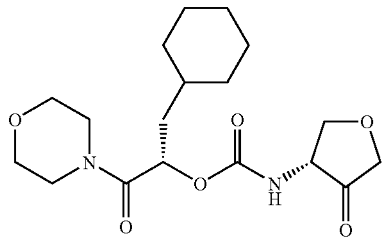 | $^1$HNMR(CD$_3$OD, 400MHz) δ 5.28-5.23(m, 2H), 4.11-3.95(m, 2H), 3.89-3.79(m, 2H), 3.72-3.44(m, 9H), 1.80(d, J=12Hz, 1H), 1.71-1.62(m, 5H), 1.47-1.44 (m, 2H), 1.3-1.13(m, 3H), 1.02-0.90(m, 2H).HPLC-MS calculated for C$_{18}$H$_{28}$ N$_2$O$_6$(M+H$^+$) 369.2, found, 369.4. |
| 29 | 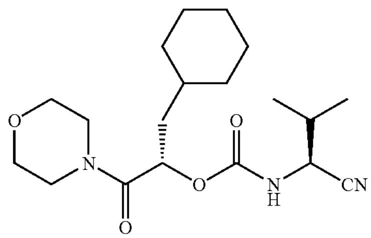 | HPLC-MS calculated for C$_{19}$H$_{31}$N$_3$O$_4$(M+H$^+$)=366.2, found 366.4. |
| 30 | 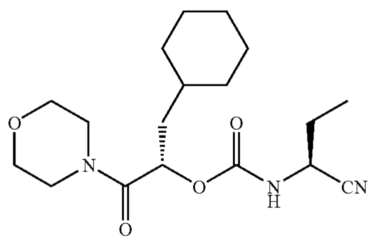 | HPLC-MS calculated for C$_{18}$H$_{29}$N$_3$O$_4$(M+H$^+$)=352.2, found 352.4. |
| 31 | 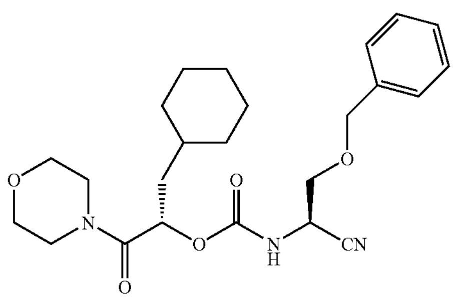 | HPLC-MS calculated for C$_{24}$H$_{33}$N$_3$O$_5$(M+H$^+$)=444.3, found 444.5. |
| 32 | 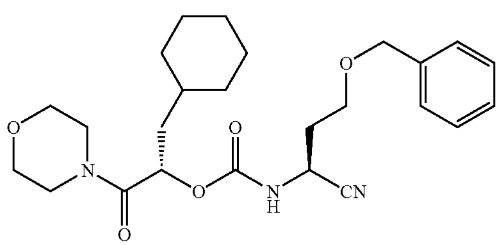 | HPLC-MS calculated for C$_{25}$H$_{35}$N$_3$O$_5$(M+H$^+$)=458.3, found 458.5. |
| 33 | 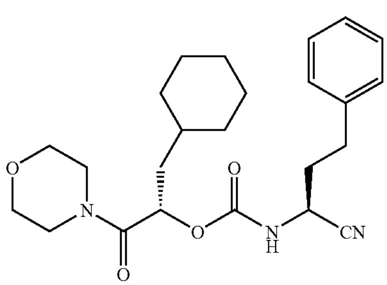 | HPLC-MS calculated for C$_{24}$H$_{33}$N$_3$O$_5$(M+H$^+$)=428.3, found 428.5. |

TABLE 1-continued

| Compound Number | Structure | Physical Data<br>$^1$H NMR 400 MHz (CDCl$_3$)<br>and/or MS (m/z) |
|---|---|---|
| 34 | 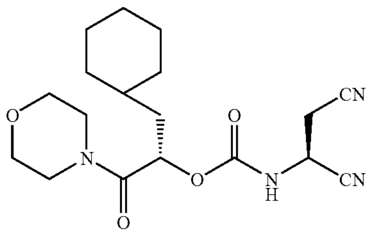 | HPLC-MS found for<br>C$_{18}$H$_{26}$N$_4$O$_4$(M+H$^+$)=363.4. |
| 35 | 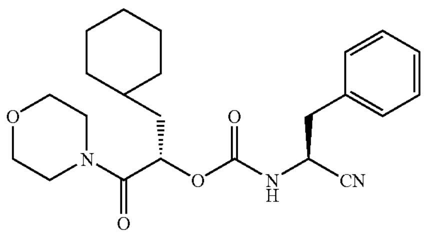 | HPLC-MS found for<br>C$_{23}$H$_{31}$N$_3$O$_4$<br>(M+H$^+$)=414.5. |
| 36 | 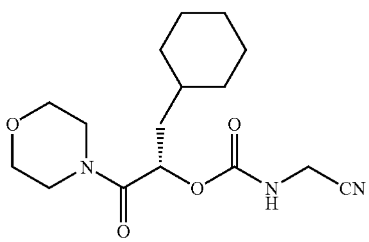 | $^1$HNMR(DMSO) δ(ppm) 8.10(m, 1H),<br>5.20(m,<br>1H), 4.01(d, 2H);<br>3.51(m, 4H), 3.38(m, 4H); 1.72(m,<br>1H);1.53(m, 5H); 1.40(m, 2H);<br>1.10(m, 3H); 0.86(m, 2H); LCMS<br>324.4(M+H)$^+$). |
| 37 | 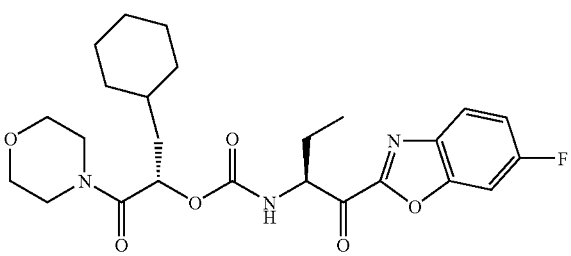 | $^1$HNMR(CDCl$_3$, 400MHz) δ<br>0.79-1.03(m, 2H), 1.02(dd, 3H, J=<br>7.5, 7.5), 1.08-1.29(m, 3H),<br>1.39-1.48(m, 2H), 1.40-1.93(m,<br>7H), 2.09-2.20(m, 1H), 3.40-3.47<br>(m, 1H), 3.52-3.58(m, 2H), 3.60-<br>3.76(m, 5H), 5.31(dd, 1H, J=<br>2.9, 10.1Hz), 5.38(ddd, 1H, J=<br>4.9, 8.0, 13.0Hz), 5.72(d, 1H, J=<br>10.3Hz), 7.23(ddd, 1H, J=2.4,<br>9.2, 11.5Hz), 7.36(dd, 1H, J=<br>2.3, 7.7Hz), 7.86(dd, 1H, J=4.8,<br>8.9Hz); HPLC-MS calculated for<br>C$_{25}$H$_{32}$FN$_3$O$_6$(M+H$^+$) 490.2,<br>found 490.4. |
| 38 | 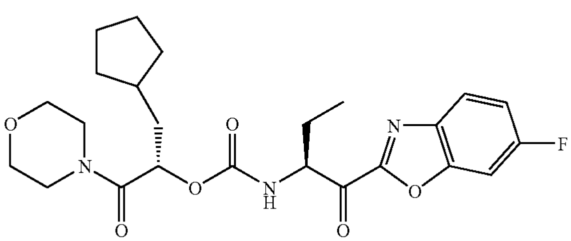 | $^1$HNMR(CDCl$_3$, 400MHz) δ1.02<br>(dd, 3H, J=7.5, 7.5), 0.78-1.08<br>(m, 2H), 1.45-1.70(m, 5H), 1.70-<br>1.96(m, 5H), 2.08-2.20(m, 1H),<br>3.43-3.77(m, 8H), 5.25(dd, 1H, J=<br>4.1, 9.0Hz), 5.36(ddd, 1H, J=<br>4.9, 8.0, 12.9Hz), 5.76(d, 1H, J=<br>8.3Hz), 7.23(ddd, 1H, J=2.4,<br>9.1, 11.5Hz), 7.36(dd, 1H, J=<br>2.3, 7.7Hz), 7.86(dd, 1H, J=4.9,<br>8.9Hz); HPLC-MS calculated for<br>C$_{24}$H$_{30}$FN$_3$O$_6$(M+H$^+$) 476.2,<br>found 476.4. |

TABLE 1-continued

| Compound Number | Structure | Physical Data $^1$H NMR 400 MHz (CDCl$_3$) and/or MS (m/z) |
|---|---|---|
| 39 | 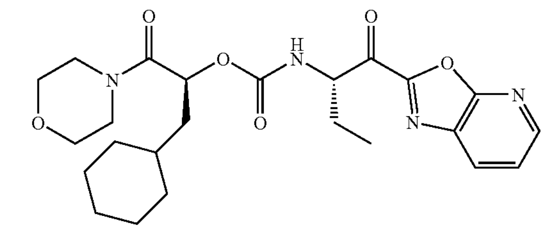 | HPLC-MS calculated for C$_{24}$H$_{32}$N$_4$O$_6$(M+H$^+$)=473.2, found 473.5. |
| 40 | 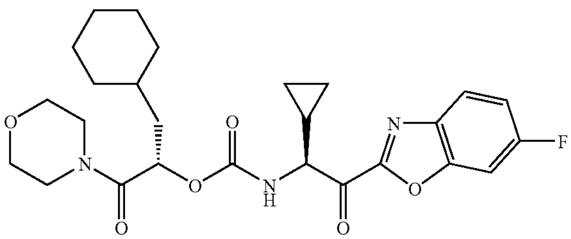 | $^1$HNMR(CDCl$_3$, 400MHz) δ 0.28-0.43(m, 3H), 0.51-0.78(m, 3H), 0.82-1.10(m, 3H), 1.14-1.24 (m, 2H), 1.37-1.60(m, 7H), 3.12-3.52(m, 8H), 4.59-4.66(m, 1H), 5.06(dd, 1H, J=2.3, 10.1Hz), 5.57(d, 1H, J=7.0Hz), 7.01(ddd, 1H, J=2.3, 9.1, 11.4Hz), 7.15 (dd, 1H, J=2.1, 7.6Hz), 7.64(dd, 1H, J=4.9, 7.6Hz); HPLC-MS calculated for C$_{26}$H$_{32}$N$_3$O$_6$(M+ 1 H$^+$) 502.2, found 502.5. |
| 41 | 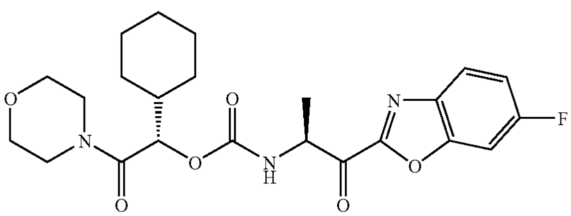 | $^1$HNMR(CDCl$_3$, 400MHz) δ 1.02-1.27(m, 5H), 1.59(d, 3H, J=7.2), 1.57-1.90(m, 6H), 3.47 3.78(m, 8H), 5.03(d, 3H, J= 7.4), 5.36-5.45(m, 1H), 5.71(d, 1H, J=7.7Hz), 7.24(ddd, 1H, J= 2.3. 9.1, 11.4Hz), 7.37(dd, 1H, J= 2.3, 7.6Hz), 7.86(dd, 1H, J= 4.9, 8.9Hz); HPLC-MS calculated for C$_{23}$H$_{28}$FN$_3$O$_6$(M+H$^+$)462.2, found 462.5. |
| 42 | 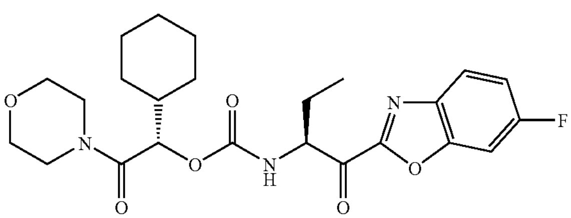 | $^1$HNMR(CDCl$_3$, 400MHz) δ1.01 (dd, 3H, J=7.5, 7.5), 0.98-0.24 (m, 4H), 1.56-1.90(m, 8H), 2.06-2.20(m, 1H), 3.48-3.78(m, 8H), 5.03(d, 1H, J=7.5Hz), 5.35(ddd, 1H, J=4.9, 8.0, 12.9Hz), 5.70(d, 1H, J=8.4Hz), 7.24(ddd, 1H, J= 2.4, 9.2, 11.5Hz), 7.36(dd, 1H, J= 2.2, 7.7Hz), 7.86(dd, 1H, J= 4.8, 8.9Hz); HPLC-MS calculated for C$_{24}$H$_{30}$FN$_3$O$_6$(M+H$^+$)476.2, found 476.5. |
| 43 | 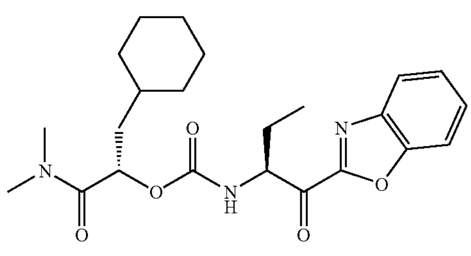 | LCMS:430.5(M+H)$^+$. |
| 44 | 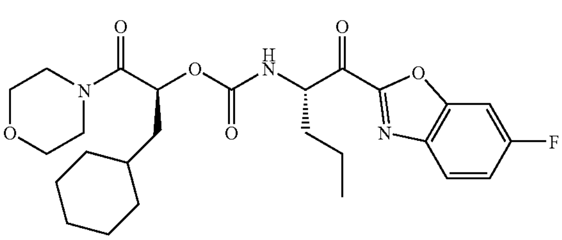 | HPLC-MS calculated For C$_{26}$H$_{34}$FN$_3$O$_6$(M+H$^+$)=504.2, found 504.5. |

TABLE 1-continued

| Compound Number | Structure | Physical Data<br>¹H NMR 400 MHz (CDCl₃)<br>and/or MS (m/z) |
|---|---|---|
| 45 | 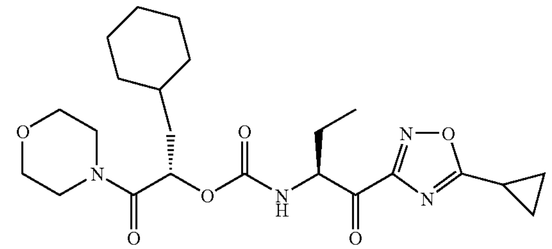 | ¹HNMR(CDCl₃400MHz) δ 0.79-0.95(m, 2H), 0.96(dd, 3H), J= 7.4, 7.4), 1.07-1.38(m, 9H), 1.49-1.50(m, 2H), 1.68-1.83(m, 6H), 1.97-2.10(m, 1H), 2.24-2.52 (m, 1H), 3.38-3.48(m, 1H), 3.49-3.59(m, 2H), 3.59-3.77(m, 5H), 5.16(ddd, 1H, J=4.9, 7.8, 12.7 Hz), 5.26-5.32(m, 1H), 5.64(d, 1H), J=8.2Hz); HPLC-MS calculated for C₂₃H₃₄N₄O₆(M+ H⁺)463.3, found 463.5. |
| 46 | 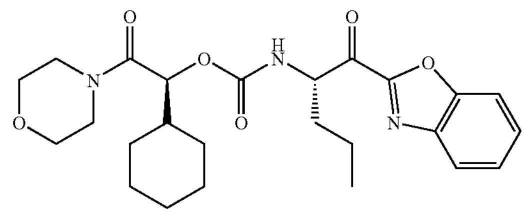 | HPLC-MS calculated for C₂₅H₃₃N₃O₆(M+H⁺)=472.2, found 472.5. |
| 47 | 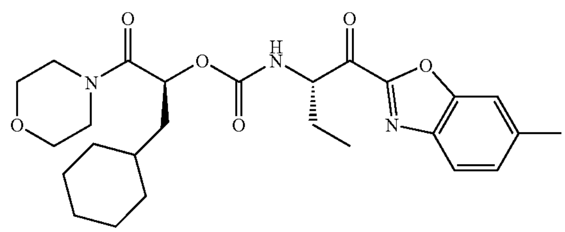 | HPLC-MS calculated for C₂₆H₃₅N₃O₆(M+H⁺)=486.3, found 486.5. |
| 48 | 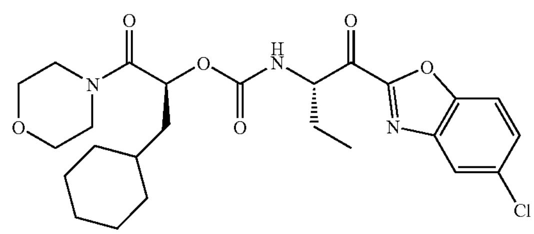 | HPLC-MS calculated for C₂₅H₃₂ClN₃O₆(M+H⁺)=506.2, found 506.4. |
| 49 | 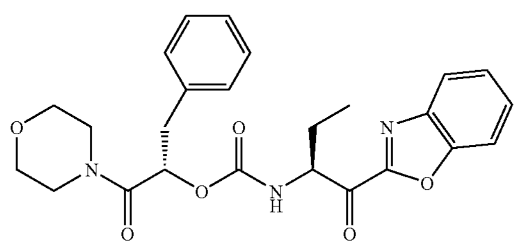 | LCMS:466.4(M+H)⁺. |
| 50 | 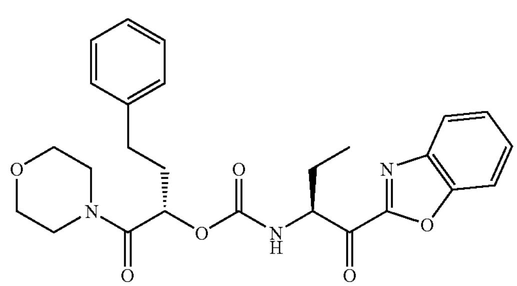 | LCMS:480.5(M+H)⁺. |

TABLE 1-continued

| Compound Number | Structure | Physical Data $^1$H NMR 400 MHz (CDCl$_3$) and/or MS (m/z) |
|---|---|---|
| 51 | 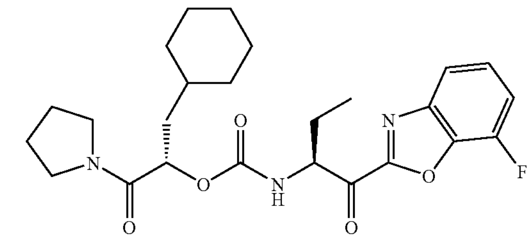 | LCMS:474.5(M+H)$^+$. |
| 52 | 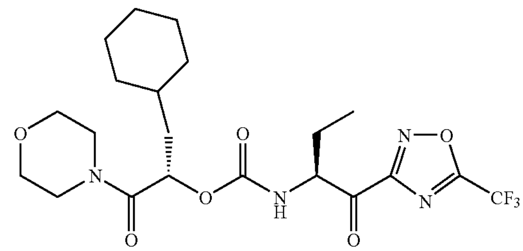 | $^1$HNMR(CDCl$_3$, 400MHz) δ 0.80-1.03(m, 3H), 1.02(dd, 3H, J=7.4, 7.4), 1.07-1.31(m, 6H), 1.38-1.50(m, 2H), 1.52-1.88(m, 3H), 2.01-2.13(m, 1H), 3.38-3.78 (m, 8H), 5.10(ddd, 1H), J=5.0, 7.6, 12.6Hz), 5.27-5.33(m, 1H), 5.77(d, 1H, J=7.6Hz); HPLC-MS calculated for C$_{21}$H$_{29}$F$_3$N$_4$O$_6$ (M+H$^+$)491.2, found 491.4. |
| 53 | 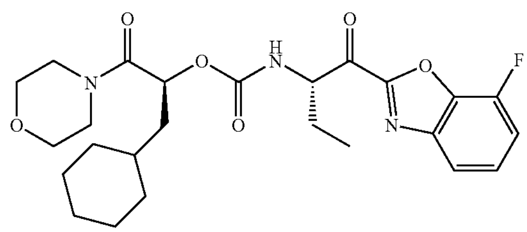 | HPLC-MS calculated for C$_{25}$H$_{32}$FN$_3$O$_6$(M+H$^+$)=490.2, found 490.5. |
| 54 | 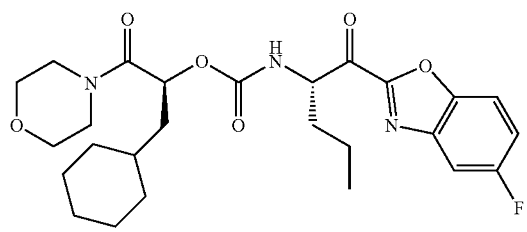 | HPLC-MS calculated for C$_{26}$H$_{34}$FN$_3$O$_6$(M+H$^+$)=504.2, found 504.2. |
| 55 | 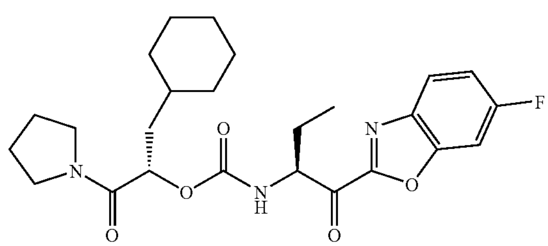 | LCMS:474.5(M+H)$^+$. |
| 56 | 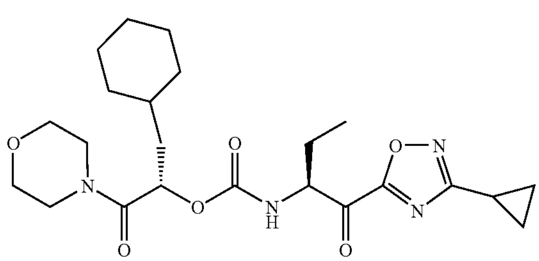 | 1HNMR(400MHz, CDCl$_3$) δ 5.63(d, J=8.0Hz, 1H), 5.29(m, 1H), 5.13(m, 1H), 3.69(m, 7H), 3.54(m, 3H), 3.45(m, 1H), 2.20 (m, 1H), 2.04(m, 1H), 1.65-1.80 (m, 7H), 1.43(m, 2H), 1.24(m, 2H), 1.08-1.18(m, 3H), 0.98(t, J=7.4Hz, 3H), 0.88(m, 1H);LC/MS calcd. for [M+H]$^+$C$_{23}$H$_{35}$N$_4$O$_6$: 463.5472, found: 463.2. |

TABLE 1-continued

| Compound Number | Structure | Physical Data $^1$H NMR 400 MHz (CDCl$_3$) and/or MS (m/z) |
|---|---|---|
| 57 | 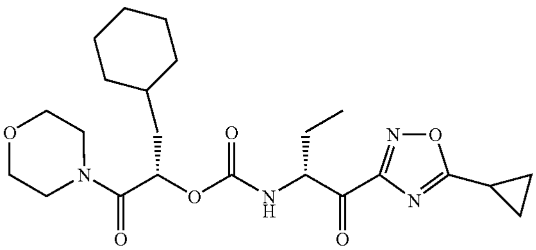 | HPLC-MS for C$_{23}$H$_{34}$N$_4$O$_6$(M+H$^+$) 463.3. |
| 58 | 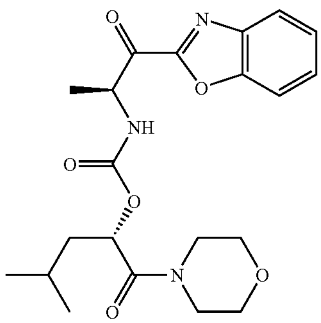 | HPLC-MS for C$_{22}$H$_{29}$N$_3$O$_6$(M+H$^+$) 432.2. |
| 59 | 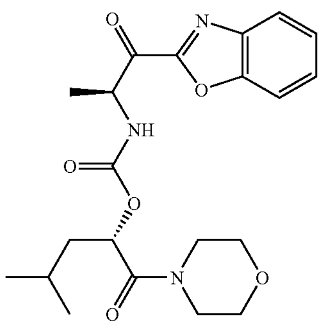 | HPLC-MS for C$_{21}$H$_{27}$N$_3$O$_6$(M+H$^+$) 418.2. |
| 60 | 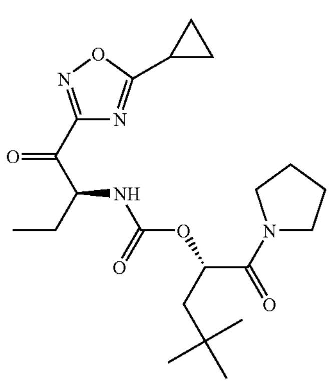 | $^1$HNMR(CDCl$_3$, 600MHz) δ 5.64(d, J=8.1Hz, 1H), 5.20-5.18 (m, 1H), 5.14-5.11(m, 1H), 3.74-3.70(m, 1H), 3.58-3.54(m, 1H), 2.30-2.26(m, 1H), 2.08-1.95(m, 3H), 1.92-1.82(m, 4H), 1.79-1.72(m, 1H), 1.46(d, J=15Hz, 1H), 1.36-1.33(m, 2H), 1.32-1.29 (m, 2H), 1.00-0.94(s, 12H). HPLC-MSforC$_{21}$H$_{32}$N$_4$O$_5$(M+H$^+$) 421.2. |

TABLE 1-continued

| Compound Number | Structure | Physical Data<br>$^1$H NMR 400 MHz (CDCl$_3$)<br>and/or MS (m/z) |
|---|---|---|
| 61 | 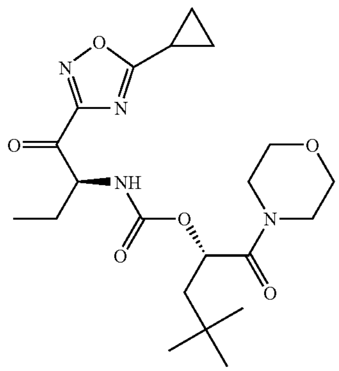 | $^1$HNMR(CDCl$_3$, 600MHz) δ 5.62(d, J=8.2Hz, 1H), 5.36(dd, J=10, 1.9Hz, 1H), 5.16-5.12(m, 1H), 3.76-3.67(m, 5H), 3.62-3.46 (m, 4H), 2.31-2.27(m, 1H), 2.09-2.02(m, 1H), 1.87(dd, J=15, 10 Hz, 1H), 1.80-1.72(m, 1H), 1.49 (dd, J=15, 1.9Hz, 1H), 1.36-1.30 (m, 4H), 0.98(s, 12).HPLC-MS for C$_{21}$H$_{32}$N$_4$O$_6$(M+H$^+$) 437.2. |

Cathepsin S Assay

Kinetic measurements are performed in a total reaction volume of 30 μl in 384-well microtiter plates. Cathepsin S, at a final concentration of 0.3-3 nM (active site), is incubated with a compound of the invention at twelve varying concentrations in a buffer containing 100 mM NaAc (pH5.5), 1 mM EDTA, 100 mM NaCl, 0.01% Brij-35 for 20 minutes at room temperature. Control reactions in the absence of inhibitor are performed in replicates of 24. The reactions are initiated by adding the substrate, acetyl-histidine-proline-valine-lysine-amino carbamoyl coumarin, to a final concentration of 50 μM. The rate of substrate hydrolysis is measured by monitoring the increase in fluorescence at an excitation wavelength of 380 nm and an emission wavelength of 450 nm that results from cleavage of the aniline bond in the substrate by the enzyme. The apparent inhibition constants for the compounds are determined from the enzyme progress curves and are then used to calculate the inhibition constants for competitive inhibitors.

Cathepsin K Assay

Kinetic measurements are performed in a total reaction volume of 30 μl in 384-well microtiter plates. Cathepsin K, at a final concentration of 3.5 nM (active site), is incubated with the compounds at twelve varying concentrations in a buffer containing 100 mM NaAc (pH5.5), 1 mM EDTA, 100 mM NaCl, 0.01% Brij-35 for 20 minutes at room temperature. Control reactions in the absence of inhibitor are performed in replicates of 24. The reactions are initiated by adding the substrate, acetyl-lysine-histidine-proline-lysine-amino carbamoyl coumarin, to a final concentration of 40 μM. The rate of substrate hydrolysis is measured by monitoring the increase in fluorescence at an excitation wavelength of 380 nm and an emission wavelength of 450 nm that results from cleavage of the aniline bond in the substrate by the enzyme. The apparent inhibition constants for the compounds are determined from the enzyme progress curves and are then used to calculate the inhibition constants for competitive inhibitors.

Cathepsin B Assay

Kinetic measurements are performed in a total reaction volume of 30 μl in 384-well microtiter plates. Cathepsin B, at a final concentration of 1.5 nM (active site), is incubated with the compounds at twelve varying concentrations in a buffer containing 100 mM NaAc (pH5.5), 1 mM EDTA, 100 mM NaCl, 0.01% Brij-35 for 20 minutes at room temperature. Control reactions in the absence of inhibitor are performed in replicates of 24. The reactions are initiated by adding the substrate, acetyl-histidine-proline-valine-lysine-amino carbamoyl coumarin, to a final concentration of 10 μM. The rate of substrate hydrolysis is measured by monitoring the increase in fluorescence at an excitation wavelength of 380 nm and an emission wavelength of 450 nm that results from cleavage of the aniline bond in the substrate by the enzyme. The apparent inhibition constants for the compounds are determined from the enzyme progress curves and are then used to calculate the inhibition constants for competitive inhibitors.

Cathepsin L Assay

Kinetic measurements are performed in a total reaction volume of 30 μl in 384-well microtiter plates. Cathepsin L, at a final concentration of 0.1 nM (active site), is incubated with the compounds at twelve varying concentrations in a buffer containing 100 mM NaAc (pH5.5), 1 mM EDTA, 100 mM NaCl, 0.01% Brij-35 for 20 minutes at room temperature. Control reactions in the absence of inhibitor are performed in replicates of 24. The reactions are initiated by adding the substrate, acetyl-histidine-lysine-phenylalanine-lysine-amino carbamoyl coumarin, to a final concentration of 20 μM. The rate of substrate hydrolysis is measured by monitoring the increase in fluorescence at an excitation wavelength of 380 nm and an emission wavelength of 450 nm that results from cleavage of the aniline bond in the substrate by the enzyme. The apparent inhibition constants for the compounds are determined from the enzyme progress curves and are then used to calculate the inhibition constants for competitive inhibitors.

Compounds of Formula I, in free form or in pharmaceutically acceptable salt form, exhibit valuable pharmacological properties, for example, as indicated by the in vitro tests described in this application. Preferred cathepsin S inhibition constants for compounds of the present invention are less than 10 μM. More preferred inhibition constants for compounds of the present invention are less than 1.0 μM. Most preferred inhibition constants for compounds of the present invention are less than 0.1 μM.

Selectivity for cathepsin S in the presence of cathepsin isozymes is determined by the ratio of the cathepsin isozyme inhibition constant of a compound of the present invention to the cathepsin S inhibition constant of the same compound. Preferred compounds of the present invention selective for cathepsin S have ratios of greater than 10. More preferred compounds of the present invention selective for cathepsin S have ratios of greater than 100. Most preferred compounds of the present invention selective for cathepsin S have ratios of greater than 1000.

For example, 2-cyclohexyl-(1S)-(morpholine-4-carbonyl)ethyl 2-(benzooxazol-2-yl)-(1S)-cyclopropyl-2-oxo-ethyl carbamate (Example 1) has an IC50 of 6.6 nM and is at least 100 fold selective for cathepsin S over cathepsin K, B and L. Further examples of activity and selectivity for the compounds of the invention are detailed in table 2.

| Example Number | Cathepsin S Ki (μM) | Cathepsin K Ki (μM) | Cathepsin L Ki (μM) | Cathepsin B Ki (μM) |
|---|---|---|---|---|
| 1 | 0.0066 | 5.163 | >23.32 | >47.5 |
| 2 | 0.4878 | >100 | >100 | >100 |
| 5 | 0.8921 | >30 | >100 | >100 |
| 8 | 0.0314 | 13.790 | >22.63 | >30 |
| 27 | 0.0008 | 0.211 | 2.03 | 5.70 |
| 39 | 0.0004 | 0.260 | 1.31 | 5.22 |
| 40 | 0.0021 | 2.130 | 15.27 | >30 |
| 42 | 0.0046 | 0.278 | 9.50 | 16.72 |
| 43 | 0.0036 | 0.250 | 4.65 | 16.00 |
| 44 | 0.0005 | 0.483 | 3.61 | 9.70 |
| 46 | 0.0016 | 0.113 | 2.21 | 4.04 |
| 47 | 0.0011 | 0.205 | 2.17 | >30 |
| 48 | 0.0028 | 0.481 | 2.75 | 1.88 |
| 54 | 0.0018 | 0.482 | 2.31 | 4.36 |
| 55 | 0.0009 | 0.188 | 3.97 | 9.09 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:

1. A compound of Formula I

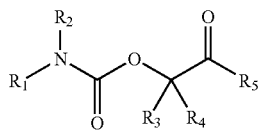

in which
$R_1$ is

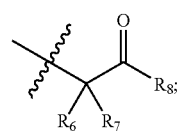

(a)

$R_6$ and $R_7$ are independently chosen from hydrogen, $C_{1-6}$alkyl, cyano-$C_{0-6}$alkyl, $C_{3-12}$cycloalkyl$C_{0-4}$alkyl and $C_{6-10}$aryl$C_{0-4}$alkyl; or $R_6$ and $R_7$ together with the carbon atom to which $R_6$ and $R_7$ are attached form $C_{3-8}$heterocycloalkyl or $C_{3-12}$cycloalkyl;

wherein any alkyl of $R_6$ and $R_7$ can optionally have a methylene replaced with an atom or group chosen from O and $S(O)_{0-2}$; wherein any aryl, heterocycloalkyl or cycloalkyl of $R_6$, $R_7$ or formed by the combination of $R_6$ and $R_7$ can be optionally substituted with 1 to 3 radicals independently selected from the group consisting of halo, hydroxy, nitro, cyano, $C_{1-6}$alkyl, $C_{1-6}$alkoxy, halo-substituted-$C_{1-6}$alkyl, halo-substituted-$C_{1-6}$alkoxy, —XC(O)OR$_{10}$, —X(S(O)$_{0-2}$R$_{10}$, —XNRS(O)$_{0-2}$R$_{10}$ and —XS(O)$_{0-2}$NR$_{10}$R$_{10}$; wherein X is a bond or $C_{1-4}$alkylene; and $R_{10}$ is independently chosen from hydrogen and $C_{1-6}$alkyl;

$R_8$ is $C_{5-10}$heteraryl$C_{0-4}$alkyl;

wherein any heteraryl of $R_8$ can be optionally substituted by 1 to 3 radicals independently chosen from halo, hydroxy, nitro, cyano, $C_{1-6}$alkyl, $C_{1-6}$alkoxy, halo-substituted-$C_{1-6}$alkyl, halo-substituted-$C_{1-6}$alkoxy, $C_{6-10}$aryl, $C_{5-10}$heteraryl, $C_{3-12}$cycloalkyl and $C_{3-8}$heterocycloalkyl; and $R_2$ is chosen from hydrogen and $C_{1-6}$alkyl;

$R_3$ and $R_4$ are independently chosen from hydrogen, $C_{1-6}$alkyl, $C_{3-12}$cycloalkyl$C_{0-4}$alkyl and $C_{6-10}$aryl$C_{0-4}$alkyl; wherein any alkyl of $R_3$ and $R_4$ can optionally have a methylene replaced with an atom or group chosen from O and $S(O)_{0-2}$; wherein any aryl or cycloalkyl of $R_3$ and $R_4$ can optionally be substituted with 1 to 3 radicals independently chosen from halo, hydroxy, nitro, cyano, $C_{1-6}$alkyl, $C_{1-6}$alkoxy, halo-substituted-$C_{1-6}$alkyl and halo-substituted-$C_{1-6}$alkoxy;

$R_5$ is $C_{3-8}$heterocycloalkyl; optionally substituted with 1 to 3 radicals independently selected from the group consisting of halo, hydroxy, nitro, cyano, $C_{1-6}$alkyl, $C_{1-6}$alkoxy, halo-substituted-$C_{1-6}$alkyl, halo-substituted-$C_{1-6}$alkoxy, —XC(O)OR$_{10}$, —X(S(O)$_{0-2}$R$_{10}$, —XNR$_{10}$S(O)$_{0-2}$R$_{10}$ and —XS(O)$_{0-2}$NR$_{10}$R$_{10}$; wherein X is a bond or $C_{1-4}$alkylene; and $R_{10}$ is independently chosen from hydrogen and $C_{1-6}$alkyl; or a pharmaceutically acceptable salt, hydrate, solvate, isomer or prodrug thereof.

2. The compound of claim 1 of Formula Ia

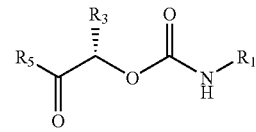

in which
$R_1$ is formula (a)

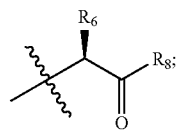

(a)

$R_6$ is chosen from hydrogen, $C_{1-6}$alkyl, cyano-$C_{0-6}$alkyl, $C_{3-12}$cycloalkyl$C_{0-4}$alkyl and $C_{6-10}$aryl$C_{0-4}$alkyl;

wherein any alkyl of $R_6$ can optionally have a methylene replaced with an atom or group chosen from O and $S(O)_{0-2}$; wherein any aryl or cycloalkyl of $R_6$ can be optionally substituted with 1 to 3 radicals independently selected from the group consisting of halo, hydroxy, nitro, cyano, $C_{1-6}$alkyl, $C_{1-6}$alkoxy, halo-substituted-$C_{1-6}$ alkyl, halo-substituted-$C_{1-6}$alkoxy, —XC(O)OR$_{10}$, —X(S(O))$_{0-2}$R$_{10}$, —XNRS(O)$_{0-2}$R$_{10}$ and —XS(O)$_{0-2}$NR$_{10}$R$_{10}$; wherein X is a bond or $C_{1-4}$alkylene; and R$_{10}$ is independently chosen from hydrogen and $C_{1-6}$alkyl;

R$_8$ is $C_{5-10}$heteraryl$C_{0-4}$alkyl;

wherein any heteroaryl of R$_8$ can be optionally substituted by 1 to 3 radicals independently chosen from halo, hydroxy, nitro, cyano, $C_{1-6}$alkyl, $C_{1-6}$alkoxy, halo-substituted-$C_{1-6}$alkyl, halo-substituted-$C_{1-6}$alkoxy, $C_{6-10}$aryl, $C_{5-10}$heteraryl, $C_{3-12}$cycloalkyl and $C_{3-8}$heterocycloalkyl; and R$_3$ is chosen from hydrogen, $C_{1-6}$alkyl, $C_{3-12}$cycloalkyl$C_{0-4}$ alkyl and $C_{6-10}$aryl$C_{0-4}$alkyl; wherein any alkyl of R$_3$ can optionally have a methylene replaced with an atom or group chosen from O and $S(O)_{0-2}$; wherein any aryl or cycloalkyl of R$_3$ can optionally be substituted with 1 to 3 radicals independently chosen from halo, hydroxy, nitro, cyano, $C_{1-6}$alkyl, $C_{1-6}$alkoxy, halo-substituted-$C_{1-6}$ alkyl and halo-substituted-$C_{1-6}$alkoxy;

R$_5$ is from $C_{3-8}$heterocycloalkyl; wherein any heterocycloalkyl of R$^5$ can be optionally substituted with 1 to 3 radicals independently selected from the group consisting of halo, hydroxy, nitro, cyano, $C_{1-6}$alkyl, $C_{1-6}$alkoxy, halo-substituted-$C_{1-6}$alkyl, halo-substituted-$C_{1-6}$alkoxy, —XC(O)OR$_{10}$, —X(S(O))$_{0-2}$R$_{10}$, —XNR$_{10}$S(O)$_{0-2}$R$_{10}$ and —XS(O)$_{0-2}$NR$_{10}$R$_{10}$; wherein X is a bond or $C_{1-4}$alkylene; and R$_{10}$ is independently chosen from hydrogen and $C_{1-6}$alkyl.

3. The compound of claim 1, in which R$_2$ and R$_4$ are both hydrogen;

R$_6$ is chosen from hydrogen, $C_{1-6}$alkyl, cyano-$C_{0-6}$alkyl, $C_{3-12}$cycloalkyl$C_{0-4}$alkyl and $C_{6-10}$aryl$C_{0-4}$alkyl; wherein any alkyl of R$_6$ can optionally have a methylene replaced with an atom or group chosen from O and $S(O)_{0-2}$; wherein any aryl or cycloalkyl of R$_6$ can be optionally substituted with 1 to 3 radicals independently selected from halo;

R$_7$ is hydrogen;

R$_8$ is $C_{5-10}$heteraryl optionally substituted by 1 to 3 radicals independently chosen from halo, $C_{1-6}$alkyl, halo-substituted-$C_{1-6}$alkyl, $C_{6-10}$aryl, $C_{5-10}$heteraryl, $C_{3-12}$cycloalkyl and $C_{3-8}$heterocycloalkyl; and R$_9$ is $C_{1-6}$alkyl;

R$_3$ is chosen from $C_{1-6}$alkyl, $C_{3-12}$cycloalkyl$C_{0-4}$alkyl and $C_{6-10}$aryl$C_{0-4}$alkyl; wherein any alkyl of R$_3$ can optionally have a methylene replaced with an atom or group chosen from O and $S(O)_{0-2}$;

R$_5$ is $C_{3-8}$heterocycloalkyl.

4. The compound of claim 3, in which R$_6$ is selected from the group consisting of hydrogen, methyl, ethyl propyl, iso-propyl, cyclopropyl, cyanomethyl, 2-chloro-benzyloxymethyl, benzyloxymethyl, benzyloxyethyl, phenethyl and benzyl.

5. The compound of claim 3, in which R$_8$ is benzooxazol-2-yl, benzothiazol-2-yl, [1,2,4]oxadiazol-3-yl, [1,2,4]oxadiazol-5-yl and oxazolo[5,4-b]pyridin-2-yl; wherein any heteroaryl of R$_8$ is optionally substituted by 1 to 3 radicals independently chosen from halo, ethyl, phenyl, cyclopropyl and trifluoromethyl.

6. The compound of claim 3, in which R$_3$ is selected from cyclohexyl-methyl, cyclopentyl-methyl, benzyl-sulfonyl-methyl, cyclohexyl-ethyl, phenyl, iso-butyl, t-butyl-methyl, cyclohexyl, benzyl, and phenethyl; and R$_5$ is chosen from morpholino, piperidinyl and pyrrolidinyl.

7. The compound of claim 6, selected from the group consisting of 2-cyclohexyl-(1S)-(morpholine-4-carbonyl) ethyl 2-(benzoxazol-2-yl)-(1S)-cyclopropyl-2-oxo-ethyl carbamate, 2-phenylmethanesulfonyl-(1R)-(morpholine-4-carbonyl)ethyl 2-(benzoxazol-2-yl)-(1S)-methyl-2-oxo-ethyl carbamate, 2-cyclohexyl-(1S)-(morpholine-4-carbonyl) ethyl (1S)-(5-ethyl-[1,2,4]oxadiazole-3-carbonyl)propyl carbamate, 2-cyclohexyl-(1S)-(morpholine-4-carbonyl)ethyl (1S)-(5-phenyl-[1,2,4]oxadiazole-3-carbonyl)propyl carbamate, 2-cyclohexyl-(1S)-(morpholine-4-carbonyl)ethyl 4-oxo-tetrahydro-furan-(3S)-yl carbamate, (S)-1-tert-butoxycarbonyl-4-cyano-4-(1-cyclohexylmethyl-2-morpholin-4-yl-2-oxo-ethoxycarbonylamino)-piperidine, (S)-4-cyano-4-(1-cyclohexylmethyl-2-morpholin-4-yl-2-oxo-ethoxycarbonylamino)-1-methyl-piperidine, (1S)-cyclohexylmethyl-2-morpholin-4-yl-2-oxo-ethyl 2-(2-chloro-benzyloxy)-(1R)-cyano-ethyl carbamate, 2-cyclohexyl-(1S)-(morpholine-4-carbonyl)ethyl 2-(benzoxazol-2-yl)-(1S)-methyl-2-oxo-ethyl carbamate, 2-cyclohexyl-(1S)-(morpholine-4-carbonyl)ethyl (1S)-(benzoxazole-2-carbonyl)-propyl carbamate, 2-cyclohexyl-(1S)-(morpholine-4-carbonyl)ethyl (1S)-(benzoxazole-2-carbonyl)-butyl carbamate, 2-cyclohexyl-(1S)-(morpholine-4-carbonyl)ethyl 2-(5-fluoro-benzoxazol-2-yl)-(1S)-methyl-2-oxo-ethyl carbamate, 2-cyclohexyl-(1S)-(morpholine-4-carbonyl)ethyl 2-(6-fluoro-benzoxazol-2-yl)-(1S)-methyl-2-oxo-ethyl carbamate, 2-cyclohexyl-(1S)-(morpholine-4-carbonyl)ethyl (1S)-(benzoxazole-2-carbonyl)-2-methyl-propyl carbamate, 2-cyclopentyl-(1S)-(morpholine-4-carbonyl)ethyl (1S)-(benzoxazole-2-carbonyl)-propyl carbamate, 2-cyclohexyl-(1S)-(morpholine-4-carbonyl) ethyl (1S)-(benzothiazole-2-carbonyl)-propyl carbamate, 2-cyclohexyl-(1S)-(morpholine-4-carbonyl)ethyl (1S)-(benzothiazole-2-carbonyl)-ethyl carbamate, 2-phenylmethanesulfonyl-(1R)-(morpholine-4-carbonyl)ethyl (1S)-(benzoxazole-2-carbonyl)-propyl carbamate, 3-cyclohexyl-(1S)-(morpholine-4-carbonyl)propyl (1S)-(benzoxazole-2-carbonyl)-ethyl carbamate, 3-cyclohexyl-(1S)-(morpholine-4-carbonyl)propyl (1S)-(benzoxazole-2-carbonyl)-propyl carbamate, (1S)-(morpholine-4-carbonyl)-1-phenyl-methyl (1S)-(benzoxazole-2-carbonyl)-propyl carbamate, 3,3-dimethyl-(1S)-(morpholine-4-carbonyl)-butyl (1S)-(benzoxazole-2-carbonyl)-propyl carbamate, (1S)-cyclohexyl-1-(morpholine-4-carbonyl)-methyl (1S)-(benzoxazole-2-carbonyl)-propyl carbamate, (1S)-cyclohexylmethyl-2-oxo-2-(piperidin-1-yl)-ethyl (1S)-(benzoxazole-2-carbonyl)-ethyl carbamate, (1S)-cyclohexylmethyl-2-oxo-2-(pyrrolidin-1-yl)-ethyl 2-(benzoxazol-2-yl)-(1S)-cyclopropyl-2-oxo-ethyl carbamate, (1S)-cyclohexylmethyl-2-oxo-2-(pyrrolidin-1-yl)-ethyl (1S)-(benzoxazole-2-carbonyl)-propyl carbamate, (1S)-cyclohexylmethyl-2-oxo-2-(pyrrolidin-1-yl)-ethyl (1S)-(benzoxazole-2-carbonyl)-butyl carbamate, 2 cyclohexyl-(1S)-(morpholine-4-carbonyl)ethyl (1S)-(6-fluoro-benzoxazole-2-carbonyl)-propyl carbamate, 2-cyclopentyl-(1S)-(morpholine-4-carbonyl)ethyl (1S)-(6-fluoro-benzoxazole-2-carbonyl)-propyl carbamate, 2-cyclohexyl-(1S)-(morpholine-4-carbonyl)ethyl (1S)-(oxazolo[5,4-b]pyridine-2-carbonyl)-propyl carbamate, 2-cyclohexyl-(1S)-(morpholine-4-carbonyl)ethyl (1S)-cyclopropyl-2-(6-fluoro-benzoxazol-2-yl)-2-oxo-ethyl carbamate, (1S)-cyclohexyl-1-(morpholine-4-carbonyl)methyl (1S)-(6-fluoro-benzoxazole-2-carbonyl)-ethyl carbamate, (1S)-cyclohexyl-1-(morpholine-4-carbonyl)methyl (1S)-(6-fluoro-benzoxazole-2-carbonyl)-propyl carbamate, 2 cyclohexyl-(1S)-(morpholine-4- carbonyl)ethyl (1S)-(6-fluoro-benzoxazole-2-carbonyl)-butyl carbamate, 2-cyclohexyl-(1S)-(morpholine-4-carbonyl)ethyl (1S)-(5-cyclopropyl-[1,2,4]oxadiazole-3-carbonyl)-propyl carbamate, (1S)-cyclohexyl-1-(morpholine-4-carbonyl)methyl (1S)-(benzoxazole-2-carbonyl)-butyl carbamate, 2-cyclohexyl-(1S)-(morpholine-4-carbonyl)ethyl (1S)-(6-methyl-benzoxazole-2-carbonyl)-propyl carbamate, 2-cyclohexyl-(1S)-(morpholine-4-carbonyl)ethyl (1S)-(5-chloro-benzoxazole-2-carbonyl)-propyl carbamate, (1S)-(morpholine-4-carbonyl)-2-phenyl-ethyl (1S)-(benzoxazole-2-carbonyl)-propyl carbamate, (1S)-(morpholine-4-carbonyl)-3-phenyl-ethyl (1S)-(benzoxazole-2-carbonyl)-propyl carbamate, (JS)-cyclohexylmethyl-2-oxo-2-(pyrrolidin-1-yl)-ethyl fluoro-benzoxazole-2-carbonyl)-propyl carbamate, 2-cyclohexyl-(1S)-(morpholine-4-carbonyl)ethyl (JS)-(5-trifluoromethyl-[1,2,4]oxadiazole-3-carbonyl)-propyl carbamate, 2-cyclohexyl-(1S)-(morpholine-4-carbonyl)ethyl (1S)-(7-fluoro-benzoxazole-2-carbonyl)-propyl carbamate, 2-cyclohexyl-(1S)-(morpholine-4-carbonyl)ethyl (1S)-(5-fluoro-benzoxazole-2-carbonyl)-butyl carbamate; (1S)-cyclohexylmethyl-2-oxo-2-(pyrrolidin-1-yl)-ethyl fluoro-benzoxazole-2-carbonyl)-propyl carbamate; 2-cyclohexyl-(1S)-(morpholine-4-carbonyl)ethyl (1S)-(3-cyclopropyl-[1,2,4]oxadiazole-5-carbonyl)-propyl carbamate; 2-cyclohexyl-(1S)-(morpholine-4-carbonyl)ethyl (1R)-(5-cyclopropyl-[1,2,4]oxadiazole-3-carbonyl)-propyl carbamate; [1-(benzooxazole-2-carbonyl)-propyl]-carbamic acid 3-methyl-1-(morpholine-4-carbonyl)-butyl ester; (S,S)-(2-benzooxazol-2-yl-1-methyl-2-oxo-ethyl)-carbamic acid 3-methyl-1-(morpholine-4-carbonyl)-butyl ester; (S,S)-[1-(5-cyclopropyl-[1,2,4]oxadiazole-3-carbonyl)-propyl]-carbamic acid 3,3-dimethyl-1-(pyrrolidine-1-carbonyl)-butyl ester; and (S,S)-[1-(5-cyclopropyl-[1,2,4]oxadiazole-3-carbonyl)-propyl]-carbamic acid 3,3-dimethyl-1-(morpholine-4-carbonyl)-butyl ester.

8. A pharmaceutical composition comprising a therapeutically effective amount of a compound of claim 1 in combination with a pharmaceutically acceptable excipient.

9. A method for treating a disease in an animal in which inhibition of Cathepsin S activity can prevent, inhibit or ameliorate the pathology and/or symptomology of the disease, which method comprises administering to the animal a therapeutically effective amount of a compound of claim 1.

* * * * *